US010202424B2

(12) United States Patent
Parks et al.

(10) Patent No.: US 10,202,424 B2
(45) Date of Patent: Feb. 12, 2019

(54) RECOMBINANT VIRAL VECTORS

(71) Applicant: International AIDS Vaccine Initiative, New York, NY (US)

(72) Inventors: Christopher L. Parks, New York, NY (US); Ivo Lorenz, New York, NY (US); Sanjay K. Phogat, New York, NY (US); Timothy J. Zamb, New York, NY (US)

(73) Assignee: International AIDS Vaccine Initiative, New York, NY (US)

( * ) Notice: Subject to any disclaimer, the term of this patent is extended or adjusted under 35 U.S.C. 154(b) by 0 days.

(21) Appl. No.: 15/663,867

(22) Filed: Jul. 31, 2017

(65) Prior Publication Data

US 2017/0327544 A1    Nov. 16, 2017

Related U.S. Application Data

(63) Continuation of application No. 14/972,272, filed on Dec. 17, 2015, now Pat. No. 9,802,986, which is a continuation of application No. 12/708,940, filed on Feb. 19, 2010, now abandoned.

(60) Provisional application No. 61/154,190, filed on Feb. 20, 2009.

(51) Int. Cl.
| | |
|---|---|
| *A61K 39/21* | (2006.01) |
| *C07K 14/005* | (2006.01) |
| *A61K 39/12* | (2006.01) |
| *C12N 7/00* | (2006.01) |
| *G01N 33/68* | (2006.01) |
| *A61K 39/00* | (2006.01) |

(52) U.S. Cl.
CPC ............ *C07K 14/005* (2013.01); *A61K 39/12* (2013.01); *A61K 39/21* (2013.01); *C12N 7/00* (2013.01); *G01N 33/6854* (2013.01); *A61K 39/00* (2013.01); *A61K 2039/5256* (2013.01); *C12N 2740/16051* (2013.01); *C12N 2740/16134* (2013.01); *C12N 2760/20234* (2013.01); *C12N 2760/20243* (2013.01); *C12N 2760/20251* (2013.01); *G01N 2333/162* (2013.01)

(58) Field of Classification Search
None
See application file for complete search history.

(56) References Cited

U.S. PATENT DOCUMENTS 6,497,873 B1    12/2002    Whitt et al.

OTHER PUBLICATIONS

Egan et al. Immunogenicity of Attenuated Vesicular Stomatitis Virus Vectors Expressing HIV Type 1 Env and SIV Gag Proteins: Comparison of Intranasal and Intramuscular Vaccination Routes. AIDS Research and Human Retroviruses. 2004, 20: 989-1004.*
Boritz et al. "Replication-competent rhabdoviruses with human immunodeficiency virus type 1 coats and green fluorescent protein: entry by a pH-independent pathway" Journal of Virology 1999, 73(8):6937-45.
Dey et al. "N-terminal substitutions in HIV-1 gp41 reduce the expression of non-trimeric envelope glycoproteins on the virus" Virology 2008, 372(1):187-200.
Eggink et al. "Selection of T1249-resistant human immunodeficiency virus type 1 variants" Journal of Virology 2008. 82(13):6678-88.
Haglund et al. "Expression of Human Immunodeficiency Virus Type 1 Gag Protein Precursor and Envelope Proteins from a Vesicular Stomatitis Virus Recombinant: High-Level Production of Virus-like Particles Containing HIV Envelope" Virology, Mar. 2000, 268(1):112-121.
Hammonds et al. "Gp120 stability on HIV-1 virions and Gag-Env pseudovirions is enhanced by an uncleaved Gag core" Virology 2003, 314(2):636-49.
Jeetendra et al. "The Membrane-Proximal Region of Vesicular Stomatitis Virus Glycoprotein G Ectodomain is Critical for Fusion and Virus Infectivity" Journal of Virology, Dec. 2003, 77(23):12807-12818.
Johnson, et al. "Specific Targeting to CD4+ Cells of Recombinant Vesicular Stomatitis Viruses Encoding Human Immunodeficiency Virus Envelope Proteins", Journal of Virology, Jul. 1997 71(7):5060-5068.
Khare et al. "Epitope selection from an uncensored peptide library displayed on avian leukosis virus" Virology 2003, 315:313-321.
Llewellyn et al. "Growth and molecular evolution of vesicular stomatitis serotype New Jersey in cells derived from its natural insect-host: evidence for natural adaptation" Virus Research 2002. 89(1 ):65-73.
Luo et al., "Induction of Neutralizing Antibody against Human Immunodeficiency Virus Type I (HIV-I) by Immunization with gp41 Membrane-Proximal External Region (MPER) Fused with Porcine Endogenous Retrovirus (PERV) p15E Fragment", Vaccine, Jan. 2006, 24(4):435-442.
Montero et al., "The Membrane-Proximal External Region of the Human Immunodeficiency Virus Type 1 Envelope: Dominant Site of Antibody Neutralization and Target for Vaccine Design", Microbiology and Molecular Biology Reviews, Mar. 2008, 72(1):54-84.
Ooi et al. "Use of superparamagnetic beads for the isolation of a peptide with specificity to cymbidium mosaic virus" Journal of Virological Methods, Sep. 2006, 136(1-2):160-5, Epub Jun. 16, 2006.

(Continued)

*Primary Examiner* — Nianxiang Zou
(74) *Attorney, Agent, or Firm* — Duane Morris LLP; Thomas J. Kowalski; Deborah L. Lu

(57) ABSTRACT

The present relation relates to recombinant vesicular stomatitis virus for use as prophylactic and therapeutic vaccines for infectious diseases of AIDS. The present invention encompasses the preparation and purification of immunogenic compositions which are formulated into the vaccines of the present invention.

11 Claims, 29 Drawing Sheets

Specification includes a Sequence Listing.

(56) References Cited

OTHER PUBLICATIONS

Owens, et al. "Cytoplasmic Domain Requirement for Incorporation of a Foreign Envelope Protein into Vesicular Stomatitis Virus" Journal of Virology, Jan. 1993, 67(1):360-365.
Riedel et al. "Cell surface expression of fusogenic vesicular stomatitis virus G protein from cloned Cdna" The EMBO Journal 1984 3(7):1477-83.
Robinson et al. "The Membrane-Proximal Stem Region of Vesicular Stomatitis Virus G Protein Confers Efficient Virus Assembly" Journal of Virology, Mar. 2000, 74(5):2239-2246.

* cited by examiner

FIG. 1A
FIG. 1B
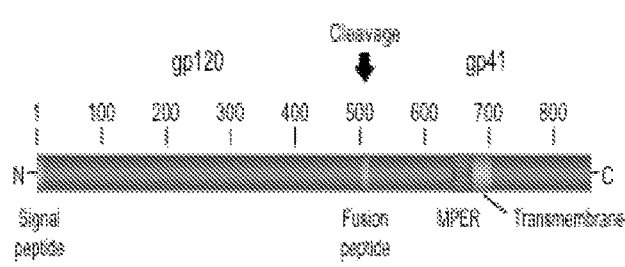
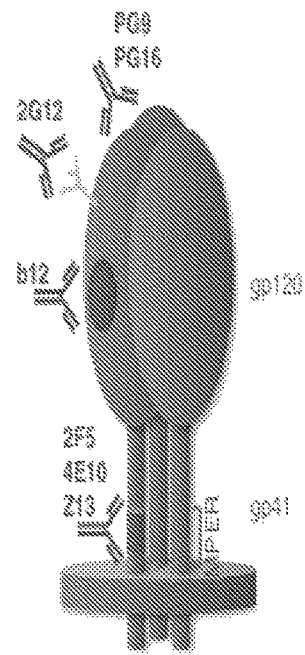

HIV-1 JRFL    Q$_{658}$ELLELDKWASLWNWFDITNWLWYIK IFIM
                          MPER              TM

VSV Indiana   E$_{447}$SLFFGDTGLSKNPIELVEGWFSSWK SSIA
                          Stem              TM ...SGELLELDKWASL...
              ...ESLFFGDTGLSKNPIELVE...
                        ↓
VSV G-2F5-Ins  ...ESLFFGDTGSGELLELDKWASLGLSKNPIELVE...       } Insertion (with linker aa)

...ELLELDKWASLWNWFDITN...
              ...SKNPIELVEGWFSSWK...
                        ↓
VSV G-2F5-Sub  ...SKNPIELLELDKWASLWNWFSSWK...

...DITNWLWYIK...
              ...ELVEGWFSSWKSSIA...                          } Substitution
                        ↓
VSV G-4E10-Sub ...VEGDITNWLWYIKSSIA...

VSV G-2F5-4E10-Sub  ...SKNPIELLELDKWASLWNDITNWLWYIKSSIA...

Mock     VSV G     VSV G-2F5-Ins

VSV G-2F5-Sub     VSV G-4E10-Sub     VSV G-2F5-4E10-Sub

| | N | P | M | G | L |

G-Stem molecule
displaying an epitope*

↑ Vaccinate
↑ Blood samples

Anti-Env ELISA
↓
Pseudovirus neutralization
Anti-VSV responses (Western blot)
Anti-Env responses (Western blot)
↓
Expanded pseudovirion neutralization testing (Monogram)

| Vaccine | Animal # |
|---------|----------|
| rVSV-env1 | 8 |
| rVSV-env2 | 8 |
| rVSV-env3 | 8 |
| Control | 4-6 |

FIG. 25

```
   1 tcaatattgg ccattagcca tattattcat tggttatata gcataaatca atattggcta
  61 ttggccattg catacgttgt atctatatca taatatgtac atttatattg gctcatgtcc
 121 aatatgaccg ccatgttggc attgattatt gactagttat taatagtaat caattacggg
 181 gtcattagtt catagcccat atatggagtt ccgcgttaca taacttacgg taaatggccc
 241 gcctggctga ccgcccaacg accccgccc attgacgtca ataatgacgt atgttcccat
 301 agtaacgcca ataggactt tccattgacg tcaatgggtg gagtatttac ggtaaactgc
 361 ccacttggca gtacatcaag tgtatcatat gccaagtccg cccctattg acgtcaatga
 421 cggtaaatgg cccgcctggc attatgccca gtacatgacc ttacgggact ttcctacttg
 481 gcagtacatc tacgtattag tcatcgctat taccatggtg atgcggtttt ggcagtacac
 541 caatgggcgt ggatagcggt ttgactcacg gggatttcca agtctccacc ccattgacgt
 601 caatgggagt ttgttttggc accaaaatca acgggacttt ccaaaatgtc gtaacaactg
 661 cgatcgcccg ccccgttgac gcaaatgggc ggtaggcgtg tacggtggga ggtctatata
 721 agcagagctc gtttagtgaa ccgtcagatc actagaagct ttattgcggt agtttatcac
 781 agttaaattg ctaacgcagt cagtgcttct gacacaacag tctcgaactt aagctgcagt
 841 gactctctta aggtagcctt gcagaagttg gtcgtgaggc actgggcagg taagtatcaa
 901 ggttacaaga caggtttaag gagaccaata gaaactgggc ttgtcgagac agagaagact
 961 cttgcgtttc tgataggcac ctattggtct tactgacatc cactttgcct ttctctccac
1021 aggtgtccac tcccagttca attacagctc ttaaggcgag agtactcgta cgctagcctc
1081 gagaggagcc accatgaagt gcctgctgta cctggccttc ctgttcatcg gcgtgaactg
1141 caagttcacc atcgtgttcc cccacaacca gaagggcaac tggaagaacg tgcccagcaa
1201 ctaccactac tgccccagca gcagcgacct gaactggcac aacgacctga tcggcaccgc
1261 cctgcaagtc aagatgccca agagccacaa ggccatccag gccgacggct ggatgtgcca
1321 cgccagcaag tgggtgacca cctgcgactt ccggtggtac ggccccaagt acatcaccca
1381 cagcatccgc agcttcaccc caagcgtgga gcagtgcaag gagagcatcg agcagaccaa
1441 gcagggcacc tggctgaacc ccggcttccc tccacaaagc tgcggctacg ccaccgtgac
1501 cgacgccgag gccgccatcg tgcaggtgac ccctcaccac gtgctggtgg acgagtacac
1561 cggcgagtgg gtggacagcc agttcatcaa cggcaagtgc agcaacgaca tctgccccac
1621 cgtgcacaac agcaccacct ggcacagcga ctacaaagtg aagggcctgt gcgacagcaa
1681 cctgatcagc accgacatca ccttcttctc cgaggacggc gagctgagca gcctgggcaa
1741 ggagggcacc ggcttccgca gcaactactt cgcctacgag accggcgaca aggcctgcaa
1801 gatgcagtac tgcaagcact ggggcgtgcg cctgcccagc ggcgtgtggt cgagatggc
1861 cgacaaggac ctgttcgccg ccgcccgctt ccccgagtgc cccgagggca gcagcatcag
1921 cgccccaagc cagaccagcg tggacgtgag cctgatccag gacgtggagc gcatcctgga
1981 ctacagcctg tgccaggaga cctggagcaa gatccgcgcc ggcctgccca tcagccccgt
2041 ggacctgagc tacctggccc ctaagaaccc cggcaccggc ccgtgttca ccatcatcaa
2101 cggcacccct aagtacttcg agacccgcta catccgcgtg gacatcgccg ccccaatcct
2161 gagccgcatg gtgggcatga tcagcggcac caccaccgag cgcgagctgt gggacgactg
2221 ggcccccttac gaggacgtgg agatcgcc taacggcgtg ctgcgcacca gcctgggcta
2281 caagtttccc ctgtacatga tcggccacgg catgctggac agcgacctgc acctgagcag
2341 caaggccag gtgttcgagc atccccacat ccaggacgcc gccagccagc tgcccgacga
2401 cgagaccctg ttcttcggcg acaccggcct gagcaagaac cccatcgagt tcgtggaggg
2461 ctggttcagc agctggaaga gcagcatcgc cagcttcttc ttcatcatcg gcctgatcat
2521 cggcctgttc ctggtgctgc gcgtgggcat ctacctgtgc atcaagctga gcacaccaa
2581 gaagcgccag atctacaccg acatcgagat gaaccgcctg ggcaagtaaa gcggccgctt
2641 ccctttagtg agggttaatg cttcgagcag acatgataag atacattgat gagtttggac
2701 aaaccacaac tagaatgcag tgaaaaaaat gctttatttg tgaaatttgt gatgctattg
2761 ctttatttgt aaccattata agctgcaata aacaagttaa caacaacaat tgcattcatt
2821 ttatgtttca ggttcagggg gagatgtggg aggttttta aagcaagtaa aacctctaca
2881 aatgtggtaa aatccgataa ggatcgatcc gggctggcgt aatagcgaag aggcccgcac
2941 cgatcgcccct tcccaacagt tgcgcagcct gaatggcgaa tggacgcgcc ctgtagcggc
3001 gcattaagcg cggcgggtgt ggtggttacg cgcagcgtga ccgctacact tgccagcgcc
3061 ctagcgcccg ctcctttcgc tttcttccct cctttctcg ccacgttcgc cggctttccc
3121 cgtcaagctc taaatcgggg ctcccttta gggttccgat ttagtgcttt acggcaccctc
3181 gaccccaaaa aacttgatta gggtgatggt tcacgtagtg ggccatcgcc ctgatagacg
3241 gtttttcgcc ctttgacgtt ggagtccacg ttctttaata gtggactctt gttccaaact
3301 ggaacaacac tcaaccctat ctcggtctat tcttttgatt tataagggat tttgccgatt
3361 tcggcctatt ggttaaaaaa tgagctgatt taacaaaaat ttaacgcgaa ttttaacaaa
3421 atattaacgc ttacaatttc ctgatgcggt attttctcct tacgcatctg tgcggtattt
3481 cacaccgcat acgcggatct gcgcagcacc atggcctgaa ataacctctg aaagaggaac
```

FIG. 27A

```
3541 ttggttaggt accttctgag gcggaaagaa ccagctgtgg aatgtgtgtc agttagggtg
3601 tggaaagtcc ccaggctccc cagcaggcag aagtatgcaa agcatgcatc tcaattagtc
3661 agcaaccagg tgtggaaagt ccccaggctc cccagcaggc agaagtatgc aaagcatgca
3721 tctcaattag tcagcaacca tagtcccgcc cctaactccg cccatcccgc ccctaactcc
3781 gcccagttcc gcccattctc cgccccatgg ctgactaatt ttttttattt atgcagaggc
3841 cgaggccgcc tcggcctctg agctattcca gaagtagtga ggaggctttt ttggaggcct
3901 aggcttttgc aaaaagcttg attcttctga cacaacagtc tcgaacttaa ggctagagcc
3961 accatgattg aacaagatgg attgcacgca ggttctccgg ccgcttgggt ggagaggcta
4021 ttcggctatg actgggcaca acagacaatc ggctgctctg atgccgccgt gttccggctg
4081 tcagcgcagg ggcgcccggt tctttttgtc aagaccgacc tgtccggtgc cctgaatgaa
4141 ctgcaggacg aggcagcgcg gctatcgtgg ctggccacga cgggcgttcc ttgcgcagct
4201 gtgctcgacg ttgtcactga agcgggaagg gactggctgc tattgggcga agtgccgggg
4261 caggatctcc tgtcatctca ccttgctcct gccgagaaag tatccatcat ggctgatgca
4321 atgcggcggc tgcatacgct tgatccggct acctgcccat tcgaccacca agcgaaacat
4381 cgcatcgagc gagcacgtac tcggatggaa gccggtcttg tcgatcagga tgatctggac
4441 gaagagcatc aggggctcgc gccagccgaa ctgttcgcca ggctcaaggc gcgcatgccc
4501 gacggcgagg atctcgtcgt gacccatggc gatgcctgct tgccgaatat catggtggaa
4561 aatggccgct tttctggatt catcgactgt ggccggctgg gtgtggcgga ccgctatcag
4621 gacatagcgt tggctacccg tgatattgct gaagagcttg gcggcgaatg ggctgaccgc
4681 ttcctcgtgc tttacggtat cgccgctccc gattcgcagc gcatcgcctt ctatcgcctt
4741 cttgacgagt tcttctgagc gggactctgg ggttcgaaat gaccgaccaa gcgacgccca
4801 acctgccatc acgatggccg caataaaata tctttatttt cattacatct gtgtgttggt
4861 tttttgtgtg aatcgatagc gataaggatc cgcgtatggt gcactctcag tacaatctgc
4921 tctgatgccg catagttaag ccagccccga cacccgccaa cacccgctga cgcgccctga
4981 cgggcttgtc tgctcccggc atccgcttac agacaagctg tgaccgtctc cgggagctgc
5041 atgtgtcaga ggttttcacc gtcatcaccg aaacgcgcga gacgaaaggg cctcgtgata
5101 cgcctatttt tataggttaa tgtcatgata ataatggttt cttagacgtc aggtggcact
5161 tttcggggaa atgtgcgcgg aaccccatt tgtttatttt tctaaataca ttcaaatatg
5221 tatccgctca tgagacaata accctgataa atgcttcaat aatattgaaa aaggaagagt
5281 atgagtattc aacatttccg tgtcgccctt attcccttt ttgcggcatt ttgccttcct
5341 gttttgctc acccagaaac gctggtgaaa gtaaaagatg ctgaagatca gttgggtgca
5401 cgagtgggtt acatcgaact ggatctcaac agcggtaaga tccttgagag ttttcgcccc
5461 gaagaacgtt ttccaatgat gagcactttt aaagttctgc tatgtggcgc ggtattatcc
5521 cgtattgacg ccgggcaaga gcaactcggt cgccgcatac actattctca gaatgacttg
5581 gttgagtact caccagtcac agaaaagcat cttacggatg gcatgacagt aagagaatta
5641 tgcagtgctg ccataaccat gagtgataac actgcggcca acttacttct gacaacgatc
5701 ggaggaccga aggagctaac cgcttttttg cacaacatgg gggatcatgt aactcgcctt
5761 gatcgttggg aaccggagct gaatgaagcc ataccaaacg acgagcgtga ccacgatg
5821 cctgtagcaa tggcaacaac gttgcgcaaa ctattaactg gcgaactact tactctagct
5881 tcccggcaac aattaataga ctggatggag gcggataaag ttgcaggacc acttctgcgc
5941 tcggcccttc cggctggctg gtttattgct gataaatctg gagccggtga gcgtgggtct
6001 cgcggtatca ttgcagcact ggggccagat ggtaagccct cccgtatcgt agttatctac
6061 acgacgggga gtcaggcaac tatgatgaa cgaaatagac agatcgctga gataggtgcc
6121 tcactgatta agcattggta actgtcagac caagtttact catatatact ttagattgat
6181 ttaaaacttc attttaatt taaaggatc taggtgaaga tcctttttga taatctcatg
6241 accaaaatcc cttaacgtga gttttcgttc cactgagcgt cagacccgt agaaaagatc
6301 aaaggatctt cttgagatcc tttttttctg cgcgtaatct gctgcttgca aacaaaaaaa
6361 ccaccgctac cagcggtggt ttgtttgccg gatcaagagc taccaactct ttttccgaag
6421 gtaactggct tcagcagagc gcagatacca aatactgttc ttctagtgta gccgtagtta
6481 ggccaccact tcaagaactc tgtagcaccg cctacatacc tcgctctgct aatcctgtta
6541 ccagtggctg ctgccagtgg cgataagtcg tgtcttaccg ggttggactc aagacgatag
6601 ttaccggata aggcgcagcg gtcgggctga acggggggtt cgtgcacaca gcccagcttg
6661 gagcgaacga cctacaccga actgagatac ctacagcgtg agctatgaga agcgccacg
6721 cttcccgaag ggagaaaggc ggacaggtat ccggtaagcg gcagggtcgg aacaggagag
6781 cgcacgaggg agcttccagg gggaaacgcc tggtatcttt atagtcctgt cgggtttcgc
6841 cacctctgac ttgagcgtcg attttttgtga tgctcgtcag ggggggggag cctatggaaa
6901 aacgccagca acgcggcctt tttacggttc ctggcctttt gctggccttt tgctcacatg
6961 gctcgacaga tct
```

FIG. 27B

FIG. 28A
G gene 1561 bp

FIG. 28B
```
ctcgagaggagccaccATGAAGTGCCTGCTGTACCTGGCCTTCCTGTTCA
TCGGCGTGAACTGCAAGTTCACCATCGTGTTCCCCCACAACCAGAAGGGC
AACTGGAAGAACGTGCCCAGCAACTACCACTACTGCCCCAGCAGCAGCGA
CCTGAACTGGCACAACGACCTGATCGGCACCGCCCTGCAaGTCAAGATGC
CAAGAGCCACAAGGCCATCCAGGCCGACGGCTGGATGTGCCACGCCAGC
AAGTGGGTGACCACCTGCGACTTCCGgTGGTACGGCCCCAAGTACATCAC
CCACAGCATCCGCAGCTTCACCCCaAGCGTGGAGCAGTGCAAGGAGAGCA
TCGAGCAGACCAAGCAGGGCACCTGGCTGAACCCCGGCTTCCCTCCaCAa
AGCTGCGGCTACGCCACCGTGACCGACGCCGAGGCCGCCATCGTGCAGGT
GACCCCtCACCACGTGCTGGTGGACGAGTACACCGGCGAGTGGGTGGACA
GCCAGTTCATCAACGGCCAAGTGCAACGACATCTGCCCCACCGTGCAC
AACAGCACCACCTGGCACAGCGACTACAAaGTGAAGGGCCTGTGCGACAG
CAACCTGATCAGCACCGACATCACCTTCTTCtccGAGGACGGCGAGCTGA
GCAGCCTGGGCAAGGAGGGCACCGGCTTCCGCAGCAACTACTTCGCCTAC
GAGACCGGCGACAAGGCCTGCAAGATGCAGTACTGCAAGCACTGGGGCGT
GCGCCTGCCCAGCGGCGTGTGGTTCGAGATGGCCGACAAGGACCTGTTCG
CCGCCGCCCCGCTTCCCCGAGTGCCCCGAGGGCAGCAGCATCAGCGCCCCa
AGCCAGACCAGCGTGGACGTGGACCTGATCCAGGACGTGGAGCGCATCCT
GGACTACAGCCTGTGCCAGGAGACCTGGAGCAAGATCCGCGCCGGCCTGC
CCATCAGCCCCGTGGACCTGAGCTACCTGGCCCCtAAGAACCCCGGCACC
GGCCCCGTGTTCACCATCATCAACGGCACCCTGAAGTACTTCGAGACCCG
CTACATCCGCGTGGACATCGCCGCCCCaATCCTGAGCCGCATGGTGGGCA
TGATCAGCGGCACCACCACCGAGCGCGAGCTGTGGGACGACTGGGCCCCt
TACGAGGACGTGGAGATCGGCCCtAACGGCGTGCTGCGCACCAGCCTGGG
CTACAAGTTtCCCCTGTACATGATCGGCCACGGCATGCTGGACAGCGACC
TGCACCTGAGCAGCAAGGCCCAGGTGTTCGAGCAtCCCCACATCCAGGAC
GCCGCCAGCCAGCTGCCCGACGACGAGACCCTGTTCTTCGGCGACACCGG
CCTGAGCAAGAACCCCATCGAGTTCGTGGAGGGCTGGTTCAGCAGCTGGA
AGAGCAGCATCGCCAGCTTCTTCTTCATCATCGGCCTGATCATCGGCCTG
TTCCTGGTGCTGCGCGTGGGCATCTACCTGTGCATCAAGCTGAAGCACAC
CAAGAAGCGCCAGATCTACACCGACATCGAGATGAACCGCCTGGGCAAGT
AAagcggccgc
``` ness, central nervous system degeneration and pro-

SEQUENCE LISTING

```
<160> NUMBER OF SEQ ID NOS: 15

<210> SEQ ID NO 1
<211> LENGTH: 30
<212> TYPE: PRT
<213> ORGANISM: Human immunodeficiency virus 1

<400> SEQUENCE: 1

Gln Glu Leu Leu Glu Leu Asp Lys Trp Ala Ser Leu Trp Asn Trp Phe
1               5                   10                  15

Asp Ile Thr Asn Trp Leu Trp Tyr Ile Lys Ile Phe Ile Met
```

```
            20                  25                  30

<210> SEQ ID NO 2
<211> LENGTH: 30
<212> TYPE: PRT
<213> ORGANISM: Vesicular stomatitis virus

<400> SEQUENCE: 2

Glu Ser Leu Phe Phe Gly Asp Thr Gly Leu Ser Lys Asn Pro Ile Glu
1               5                   10                  15

Leu Val Glu Gly Trp Phe Ser Ser Trp Lys Ser Ser Ile Ala
            20                  25                  30

<210> SEQ ID NO 3
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Ser Gly Glu Leu Leu Glu Leu Asp Lys Trp Ala Ser Leu Gly
1               5                   10

<210> SEQ ID NO 4
<211> LENGTH: 19
<212> TYPE: PRT
<213> ORGANISM: Vesicular stomatitis virus

<400> SEQUENCE: 4

Glu Ser Leu Phe Phe Gly Asp Thr Gly Leu Ser Lys Asn Pro Ile Glu
1               5                   10                  15

Leu Val Glu

<210> SEQ ID NO 5
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Glu Ser Leu Phe Phe Gly Asp Thr Gly Ser Gly Glu Leu Leu Glu Leu
1               5                   10                  15

Asp Lys Trp Ala Ser Leu Gly Leu Ser Lys Asn Pro Ile Glu Leu Val
            20                  25                  30

Glu

<210> SEQ ID NO 6
<211> LENGTH: 19
<212> TYPE: PRT
<213> ORGANISM: Human immunodeficiency virus 1

<400> SEQUENCE: 6

Glu Leu Leu Glu Leu Asp Lys Trp Ala Ser Leu Trp Asn Trp Phe Asp
1               5                   10                  15

Ile Thr Asn

<210> SEQ ID NO 7
```

```
<211> LENGTH: 16
<212> TYPE: PRT
<213> ORGANISM: Vesicular stomatitis virus

<400> SEQUENCE: 7

Ser Lys Asn Pro Ile Glu Leu Val

```
            1               5                  10                 15
           Trp Asn Trp Phe Asp Ile Thr Asn Trp Leu Trp Tyr Ile Lys Ser Ser
                        20                  25                 30

Ile Ala
```

<210> SEQ ID NO 13
<211> LENGTH: 136
<212> TYPE: PRT
<213> ORGANISM: Vesicular stomatitis virus

<400> SEQUENCE: 13

```
Met Lys Cys Leu Leu Tyr Leu Ala Phe Leu Phe Ile Gly Val Asn Cys
 1               5                  10                  15

Lys Ala Ser Gly Tyr Lys Phe Pro Leu Tyr Met Ile Gly His Gly Met
            20                  25                  30

Leu Asp Ser Asp Leu His Leu Ser Ser Lys Ala Gln Val Phe Glu His
        35                  40                  45

Pro His Ile Gln Asp Ala Ala Ser Gln Leu Pro Asp Asp Glu Ser Leu
    50                  55                  60

Phe Phe Gly Asp Thr Gly Leu Ser Lys Asn Pro Ile Glu Leu Val Glu
65                  70                  75                  80

Gly Trp Phe Ser Ser Trp Lys Ser Ser Ile Ala Ser Phe Phe Phe Ile
                85                  90                  95

Ile Gly Leu Ile Ile Gly Leu Phe Leu Val Leu Arg Val Gly Ile His
                100                 105                 110

Leu Cys Ile Lys Leu Lys His Thr Lys Lys Arg Gln Ile Tyr Thr Asp
            115                 120                 125

Ile Glu Met Asn Arg Leu Gly Lys
        130                 135
```

<210> SEQ ID NO 14
<211> LENGTH: 6973
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 14

```
tcaatattgg ccattagcca tattattcat tggttatata gcataaatca atattggcta    60
ttggccattg catacgttgt atctatatca taatatgtac atttatattg gctcatgtcc   120
aatatgaccg ccatgttggc attgattatt gactagttat taatagtaat caattacggg   180
gtcattagtt catagcccat atatggagtt ccgcgttaca aacttacgg taaatggccc    240 gcctggctga ccgcccaacg accccgccc attgacgtca taatgacgt atgttcccat     300 agtaacgcca atagggactt tccattgacg tcaatgggtg gagtattac ggtaaactgc    360 ccacttggca gtacatcaag tgtatcatat gccaagtccg cccctattg acgtcaatga    420 cggtaaatgg cccgcctggc attatgccca gtacatgacc ttacgggact ttcctacttg    480
gcagtacatc tacgtattag tcatcgctat taccatggtg atgcggtttt ggcagtacac   540
caatgggcgt ggatagcggt ttgactcacg gggatttcca agtctccacc ccattgacgt   600
caatgggagt ttgttttggc accaaaatca acgggacttt ccaaaatgtc gtaacaactg    660
cgatcgcccg ccccgttgac gcaaatgggc ggtaggcgtg tacggtggga ggtctatata   720
agcagagctc gtttagtgaa ccgtcagatc actagaagct ttattgcggt agtttatcac    780
```

```
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaggcgag agtactcgta cgctagcctc   1080
gagaggagcc accatgaagt gcctgctgta cctggccttc ctgttcatcg gcgtgaactg   1140
caagttcacc atcgtgttcc cccacaacca aagggcaac tggaagaacg tgcccagcaa   1200
ctaccactac tgccccagca gcagcgacct gaactggcac aacgacctga tcggcaccgc   1260
cctgcaagtc aagatgccca agagccacaa ggccatccag gccgacggct ggatgtgcca   1320
cgccagcaag tgggtgacca cctgcgactt ccggtggtac ggccccaagt acatcaccca   1380
cagcatccgc agcttcaccc caagcgtgga gcagtgcaag gagagcatcg agcagaccaa   1440
gcagggcacc tggctgaacc ccggcttccc tccacaaagc tgcggctacg ccaccgtgac   1500
cgacgccgag gccgccatcg tgcaggtgac ccctcaccac gtgctggtgg acgagtacac   1560
cggcgagtgg gtggacagcc agttcatcaa cggcaagtgc agcaacgaca tctgccccac   1620
cgtgcacaac agcaccacct ggcacagcga ctacaaagtg aagggcctgt gcgacagcaa   1680
cctgatcagc accgacatca ccttcttctc cgaggacggc gagctgagca gcctgggcaa   1740
ggagggcacc ggcttccgca gcaactactt cgcctacgag accggcgaca aggcctgcaa   1800
gatgcagtac tgcaagcact ggggcgtgcg cctgcccagc ggcgtgtggt tcgagatggc   1860
cgacaaggac ctgttcgccg ccgcccgctt ccccgagtgc cccgagggca gcagcatcag   1920
cgccccaagc cagaccagcg tggacgtgag cctgatccag gacgtggagc gcatcctgga   1980
ctacagcctg tgccaggaga cctggagcaa gatccgcgcc ggcctgccca tcagcccgt   2040
ggacctgagc tacctggccc ctaagaaccc cggcaccggc cccgtgttca ccatcatcaa   2100
cggcaccctg aagtacttcg agaccgcta catccgcgtg gacatcgccg ccccaatcct   2160
gagccgcatg gtgggcatga tcagcggcac caccaccgag cgcgagctgt gggacgactg   2220
ggccccttac gaggacgtgg agatcggccc taacggcgtg ctgcgcacca gcctgggcta   2280
caagtttccc ctgtacatga tcggccacgg catgctggac agcgacctgc acctgagcag   2340
caaggcccag gtgttcgagc atccccacat ccaggacgcc gccagccagc tgcccgacga   2400
cgagaccctg ttcttcggcg acaccggcct gagcaagaac cccatcgagt tcgtggaggg   2460
ctggttcagc agctggaaga gcagcatcgc cagcttcttc ttcatcatcg gcctgatcat   2520
cggcctgttc ctggtgctgc gcgtgggcat ctacctgtgc atcaagctga gcacaccaa   2580
gaagcgccaa atctacaccg acatcgagat gaaccgcctg ggcaagtaaa gcggccgctt   2640
ccctttagtg agggttaatg cttcgagcag acatgataag atacattgat gagtttggac   2700
aaaccacaac tagaatgcag tgaaaaaaat gctttatttg tgaaatttgt gatgctattg   2760
ctttatttgt aaccattata agctgcaata aacaagttaa caacaacaat tgcattcatt   2820
ttatgtttca ggttcagggg gagatgtggg aggttttta agcaagtaa aacctctaca   2880
aatgtggtaa aatccgataa ggatcgatcc gggctgcgt aatagcgaag aggcccgcac   2940
cgatcgccct tcccaacagt tgcgcagcct gaatggcgaa tggacgcgcc ctgtagcggc   3000
gcattaagcg cggcgggtgt ggtggttacg cgcagcgtga ccgctacact tgccagcgcc   3060
ctagcgcccg ctcctttcgc tttcttccct tcctttctcg ccacgttcgc cggctttccc   3120
```

```
cgtcaagctc taaatcgggg gctcccttta gggttccgat ttagtgcttt acggcacctc   3180
gaccccaaaa aacttgatta gggtgatggt tcacgtagtg ggccatcgcc ctgatagacg   3240 gttttcgcc ctttgacgtt ggagtccacg ttctttaata gtggactctt gttccaaact   3300
ggaacaacac tcaaccctat ctcggtctat tcttttgatt tataagggat tttgccgatt   3360
tcggcctatt ggttaaaaaa tgagctgatt taacaaaaat ttaacgcgaa ttttaacaaa   3420
atattaacgc ttacaatttc ctgatgcggt attttctcct tacgcatctg tgcggtattt   3480
cacaccgcat acgcggatct cgcagcacc atggcctgaa ataacctctg aaagaggaac   3540
ttggttaggt accttctgag gcggaaagaa ccagctgtgg aatgtgtgtc agttagggtg   3600
tggaaagtcc ccaggctccc cagcaggcag aagtatgcaa agcatgcatc tcaattagtc   3660
agcaaccagg tgtggaaagt ccccaggctc cccagcaggc agaagtatgc aaagcatgca   3720
tctcaattag tcagcaacca tagtcccgcc cctaactccg cccatcccgc cctaactcc   3780 gcccagttcc gcccattctc cgccccatgg ctgactaatt tttttattt atgcagaggc   3840 cgaggccgcc tcggcctctg agctattcca gaagtagtga ggaggctttt ttggaggcct   3900
aggcttttgc aaaaagcttg attcttctga cacaacagtc tcgaacttaa ggctagagcc   3960
accatgattg aacaagatgg attgcacgca ggttctccgg ccgcttgggt ggagaggcta   4020
ttcggctatg actgggcaca acagacaatc ggctgctctg atgccgccgt gttccggctg   4080
tcagcgcagg ggcgcccggt tcttttgtc aagaccgacc tgtccggtgc cctgaatgaa   4140
ctgcaggacg aggcagcgcg gctatcgtgg ctggccacga cgggcgttcc ttgcgcagct   4200
gtgctcgacg ttgtcactga agcgggaagg gactggctgc tattgggcga agtgccgggg   4260
caggatctcc tgtcatctca ccttgctcct gccgagaaag tatccatcat ggctgatgca   4320
atgcggcggc tgcatacgct tgatccggct acctgcccat tcgaccacca agcgaaacat   4380
cgcatcgagc gagcacgtac tcggatggaa gccggtcttg tcgatcagga tgatctggac   4440
gaagagcatc aggggctcgc gccagccgaa ctgttcgcca ggctcaaggc gcgcatgccc   4500
gacggcgagg atctcgtcgt gacccatggc gatgcctgct tgccgaatat catggtggaa   4560
aatggccgct tttctggatt catcgactgt ggccggctgg gtgtggcgga ccgctatcag   4620
gacatagcgt tggctacccg tgatattgct gaagagcttg gcggcgaatg ggctgaccgc   4680
ttcctcgtgt tttacggtat cgccgctccc gattcgcagc gcatcgcctt ctatcgcctt   4740
cttgacgagt tcttctgagc gggactctgg ggttcgaaat gaccgaccaa gcgacgccca   4800
acctgccatc acgatggccg caataaaata tctttatttt cattacatct gtgtgttggt   4860
tttttgtgtg aatcgatagc gataaggatc cgcgtatggt gcactctcag tacaatctgc   4920
tctgatgccg catagttaag ccagccccga cacccgccaa cacccgctga cgcgccctga   4980
cgggcttgtc tgctcccggc atccgcttac agacaagctg tgaccgtctc cgggagctgc   5040
atgtgtcaga ggttttcacc gtcatcaccg aaacgcgcga cgcgaaggg cctcgtgata   5100 cgcctatttt tataggttaa tgtcatgata ataatggttt cttagacgtc aggtggcact   5160
tttcggggaa atgtgcgcgg aacccctatt tgtttatttt tctaaataca ttcaaatatg   5220
tatccgctca tgagacaata accctgataa atgcttcaat aatattgaaa aaggaagagt   5280
atgagtattc aacatttccg tgtcgccctt attcccttt ttgcggcatt ttgccttcct   5340
gtttttgctc acccagaaac gctggtgaaa gtaaaagatg ctgaagatca gttgggtgca   5400
cgagtgggtt acatcgaact ggatctcaac agcggtaaga tccttgagag ttttcgcccc   5460
gaagaacgtt ttccaatgat gagcactttt aaagttctgc tatgtggcgc ggtattatcc   5520
```

```
cgtattgacg ccgggcaaga gcaactcggt cgccgcatac actattctca gaatgacttg    5580
gttgagtact caccagtcac agaaaagcat cttacggatg gcatgacagt aagagaatta    5640
tgcagtgctg ccataaccat gagtgataac actgcggcca acttacttct gacaacgatc    5700
ggaggaccga aggagctaac cgcttttttg cacaacatgg gggatcatgt aactcgcctt    5760
gatcgttggg aaccggagct gaatgaagcc ataccaaacg acgagcgtga caccacgatg    5820
cctgtagcaa tggcaacaac gttgcgcaaa ctattaactg gcgaactact tactctagct    5880
tcccggcaac aattaataga ctggatggag gcggataaag ttgcaggacc acttctgcgc    5940
tcggcccttc cggctggctg gtttattgct gataaatctg gagccggtga gcgtgggtct    6000
cgcggtatca ttgcagcact ggggccagat ggtaagccct cccgtatcgt agttatctac    6060
acgacgggga gtcaggcaac tatggatgaa cgaaatagac agatcgctga gataggtgcc    6120
tcactgatta agcattggta actgtcagac caagtttact catatatact ttagattgat    6180
ttaaaacttc attttaatt taaaaggatc taggtgaaga tcctttttga taatctcatg    6240
accaaaatcc cttaacgtga gttttcgttc cactgagcgt cagaccccgt agaaaagatc    6300
aaaggatctt cttgagatcc ttttttttctg cgcgtaatct gctgcttgca acaaaaaaaa    6360
ccaccgctac cagcggtggt ttgtttgccg gatcaagagc taccaactct ttttccgaag    6420
gtaactggct tcagcagagc gcagatacca aatactgttc ttctagtgta gccgtagtta    6480
ggccaccact tcaagaactc tgtagcaccg cctacatacc tcgctctgct aatcctgtta    6540
ccagtggctg ctgccagtgg cgataagtcg tgtcttaccg ggttggactc aagacgatag    6600
ttaccggata aggcgcagcg tcgggctga acgggggtt cgtgcacaca gcccagcttg    6660
gagcgaacga cctacaccga actgagatac ctacagcgtg agctatgaga aagcgccacg    6720
cttcccgaag ggagaaaggc ggacaggtat ccggtaagcg cagggtcgg aacaggagag    6780 cgcacgaggg agcttccagg gggaaacgcc tggtatcttt atagtcctgt cgggtttcgc    6840
cacctctgac ttgagcgtcg attttttgtga tgctcgtcag ggggcggag cctatggaaa    6900 aacgccagca acgcggcctt tttacggttc ctggccttttt gctggccttt tgctcacatg    6960
gctcgacaga tct                                                        6973
```

<210> SEQ ID NO 15
<211> LENGTH: 1561
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15

```
ctcgagagga gccaccatga agtgcctgct gtacctggcc ttcctgttca tcggcgtgaa     60
ctgcaagttc accatcgtgt tcccccacaa ccagaagggc aactggaaga acgtgcccag    120
caactaccac tactgcccca gcagcagcga cctgaactgg cacaacgacc tgatcggcac    180
cgccctgcaa gtcaagatgc ccaagagcca caggccatc caggccgacg gctggatgtg    240
ccacgccagc aagtgggtga ccacctgcga cttccggtgg tacggcccca gtacatcac    300 ccacagcatc cgcagcttca ccccaagcgt ggagcagtgc aaggagagca tcgagcagac    360
caagcagggc acctggctga acccggctt ccctccacaa agctgcggct acgccaccgt    420
gaccgacgcc gaggccgcca tcgtgcaggt gaccctcac cacgtgctgg tggacgagta    480
```

```
caccggcgag tgggtggaca gccagttcat caacggcaag tgcagcaacg acatctgccc       540
caccgtgcac aacagcacca cctggcacag cgactacaaa gtgaagggcc tgtgcgacag       600
caacctgatc agcaccgaca tcaccttctt ctccgaggac ggcgagctga gcagcctggg       660
caaggagggc accggcttcc gcagcaacta cttcgcctac gagaccggcg acaaggcctg       720
caagatgcag tactgcaagc actggggcgt gcgcctgccc agcggcgtgt ggttcgagat       780
ggccgacaag gacctgttcg ccgccgcccg cttccccgag tgccccgagg gcagcagcat       840
cagcgcccca agccagacca gcgtggacgt gagcctgatc caggacgtgg agcgcatcct       900
ggactacagc ctgtgccagg agacctggag caagatccgc gccggcctgc ccatcagccc       960
cgtggacctg agctacctgg cccctaagaa ccccggcacc ggcccgtgt tcaccatcat      1020 caacggcacc ctgaagtact tcgagacccg ctacatccgc gtggacatcg ccgcccaat      1080 cctgagccgc atggtgggca tgatcagcgg caccaccacc gagcgcgagc tgtgggacga      1140
ctgggcccct tacgaggacg tggagatcgg ccctaacggc gtgctgcgca ccagcctggg      1200
ctacaagttt cccctgtaca tgatcggcca cggcatgctg gacagcgacc tgcacctgag      1260
cagcaaggcc caggtgttcg agcatcccca catccaggac gccgccagcc agctgcccga      1320
cgacgagacc ctgttcttcg gcgacaccgg cctgagcaag aaccccatcg agttcgtgga      1380
gggctggttc agcagctgga agagcagcat cgccagcttc ttcttcatca tcggcctgat      1440
catcggcctg ttcctggtgc tgcgcgtggg catctacctg tgcatcaagc tgaagcacac      1500
caagaagcgc cagatctaca ccgacatcga gatgaaccgc ctgggcaagt aaagcggccg      1560
c                                                                     1561
```

RECOMBINANT VIRAL VECTORS

INCORPORATION BY REFERENCE

This application is a Continuation of U.S. application Ser. No. 14/972,272 filed Dec. 17, 2015, now pending, which is a Continuation of U.S. application Ser. No. 12/708,940 filed Feb. 19, 2010, now abandoned and claims the benefit of priority to U.S. Provisional Patent Application No. 61/154,190 filed Feb. 20, 2009.

FEDERAL FUNDING LEGEND

This invention was supported, in part, by NIH grant number: R01-AI084840. The federal government may have certain rights to this invention.

The foregoing applications, and all documents cited therein or during their prosecution ("appln cited documents") and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

SEQUENCE LISTING

The instant application contains a Sequence Listing which has been submitted via electronically and is hereby incorporated by reference in its entirety. Said ASCII copy, created on Jun. 9, 2017, is named 43094022009.txt and is 16,852 bytes in size.

FIELD OF THE INVENTION

The present invention relates to recombinant vesicular stomatitis virus for use as prophylactic and therapeutic vaccines for infectious diseases of AIDS.

BACKGROUND OF THE INVENTION

AIDS, or Acquired Immunodeficiency Syndrome, is caused by human immunodeficiency virus (HIV) and is characterized by several clinical features including wasting syndromes, central nervous system degeneration and profound immunosuppression that results in opportunistic infections and malignancies. HIV is a member of the lentivirus family of animal retroviruses, which include the visna virus of sheep and the bovine, feline, and simian immunodeficiency viruses (SIV). Two closely related types of HIV, designated HIV-1 and HIV-2, have been identified thus far, of which HIV-1 is by far the most common cause of AIDS. However, HIV-2, which differs in genomic structure and antigenicity, causes a similar clinical syndrome.

An infectious HIV particle consists of two identical strands of RNA, each approximately 9.2 kb long, packaged within a core of viral proteins. This core structure is surrounded by a phospholipid bilayer envelope derived from the host cell membrane that also includes virally-encoded membrane proteins (Abbas et al., Cellular and Molecular Immunology, 4th edition, W.B. Saunders Company, 2000, p. 454). The HIV genome has the characteristic 5'-LTR-Gag-Pol-Env-LTR-3' organization of the retrovirus family. Long terminal repeats (LTRs) at each end of the viral genome serve as binding sites for transcriptional regulatory proteins from the host and regulate viral integration into the host genome, viral gene expression, and viral replication.

The HIV genome encodes several structural proteins. The gag gene encodes structural proteins of the nucleocapsid core and matrix. The pol gene encodes reverse transcriptase (RT), integrase (IN), and viral protease (PR) enzymes required for viral replication. The tat gene encodes a protein that is required for elongation of viral transcripts. The rev gene encodes a protein that promotes the nuclear export of incompletely spliced or unspliced viral RNAs. The vif gene product enhances the infectivity of viral particles. The vpr gene product promotes the nuclear import of viral DNA and regulates G2 cell cycle arrest. The vpu and nef genes encode proteins that down regulate host cell CD4 expression and enhance release of virus from infected cells. The env gene encodes the viral envelope glycoprotein that is translated as a 160-kilodalton (kDa) precursor (gp160) and cleaved by a cellular protease to yield the external 120-kDa envelope glycoprotein (gp120) and the transmembrane 41-kDa envelope glycoprotein (gp41), which are required for the infection of cells (Abbas, pp. 454-456). gp140 is a modified form of the Env glycoprotein, which contains the external 120-kDa envelope glycoprotein portion and the extracellular part of the gp41 portion of Env and has characteristics of both gp120 and gp41. The nef gene is conserved among primate lentiviruses and is one of the first viral genes that is transcribed following infection. In vitro, several functions have been described, including down-regulation of CD4 and MHC class I surface expression, altered T-cell signaling and activation, and enhanced viral infectivity.

HIV infection initiates with gp120 on the viral particle binding to the CD4 and chemokine receptor molecules (e.g., CXCR4, CCR5) on the cell membrane of target cells such as $CD4^+$ T-cells, macrophages and dendritic cells. The bound virus fuses with the target cell and reverse transcribes the RNA genome. The resulting viral DNA integrates into the cellular genome, where it directs the production of new viral RNA, and thereby viral proteins and new virions. These virions bud from the infected cell membrane and establish productive infections in other cells. This process also kills the originally infected cell. HIV can also kill cells indirectly because the CD4 receptor on uninfected T-cells has a strong affinity for gp120 expressed on the surface of infected cells. In this case, the uninfected cells bind, via the CD4 receptor-gp120 interaction, to infected cells and fuse to form a syncytium, which cannot survive. Destruction of $CD4^+$ T-lymphocytes, which are critical to immune defense, is a major cause of the progressive immune dysfunction that is the hallmark of AIDS disease progression. The loss of $CD4^+$ T cells seriously impairs the body's ability to fight most invaders, but it has a particularly severe impact on the defenses against viruses, fungi, parasites and certain bacteria, including mycobacteria.

Research on the Env glycoprotein has shown that the virus has many effective protective mechanisms with few vulnerabilities (Wyatt & Sodroski, Science. 1998 Jun. 19; 280(5371):1884-8). For fusion with its target cells, HIV-1 uses a trimeric Env complex containing gp120 and gp41 subunits (Burton et al., Nat Immunol. 2004 March; 5(3): 233-6). The fusion potential of the Env complex is triggered by engagement of the CD4 receptor and a coreceptor, usually CCRS or CXCR4. Neutralizing antibodies seem to work either by binding to the mature trimer on the virion surface and preventing initial receptor engagement events, or by binding after virion attachment and inhibiting the fusion process (Parren & Burton, Adv Immunol. 2001; 77:195-262). In the latter case, neutralizing antibodies may bind to epitopes whose exposure is enhanced or triggered by receptor binding. However, given the potential antiviral effects of neutralizing antibodies, it is not unexpected that HIV-1 has evolved multiple mechanisms to protect it from antibody binding (Johnson & Desrosiers, Annu Rev Med. 2002; 53:499-518).

There remains a need to express immunogens that elicit broadly neutralizing antibodies. Strategies include producing molecules that mimic the mature trimer on the virion surface, producing Env molecules engineered to better present neutralizing antibody epitopes than wild-type molecules, generating stable intermediates of the entry process to expose conserved epitopes to which antibodies could gain access during entry and producing epitope mimics of the broadly neutralizing monoclonal antibodies determined from structural studies of the antibody-antigen complexes (Burton et al., Nat Immunol. 2004 March; 5(3):233-6). However, none of these approaches have yet efficiently elicited neutralizing antibodies with broad specificity.

Citation or identification of any document in this application is not an admission that such document is available as prior art to the present application.

SUMMARY OF THE INVENTION

The current invention is based, in part, on Applicant's discovery that HIV gp41 epitopes known to elicit broadly neutralizing antibodies inserted into a viral glycoprotein are recognized by such broadly neutralizing antibodies in cells infected with the recombinant virus expressing the viral glycoprotein.

Recombinant viruses are viruses generated by introducing foreign genetic material into the genome of the virus. The genome of a virus can comprise either DNA or RNA. The genome of an RNA virus can be further characterized to be either positive-sense (plus-strand) or negative-sense (minus-strand). A plus-strand (5' to 3') viral RNA indicates that a particular viral RNA sequence can be directly translated into the desired viral proteins whereas a minus-strand (3' to 5') viral RNA must be first converted to a positive-sense by an RNA polymerase prior to translation.

In a first embodiment, the invention relates to a recombinant vesicular stomatitis virus (VSV) vector wherein the gene encoding the VSV surface glycoprotein G (VSV G) may be functionally replaced by HIV Env. The HIV Env may be recognized by antibodies PG9, PG16, 2G12, b12, 2F5, 4E10 or Z13 or other antibodies, including potent broadly neutralizing trimer-specific antibodies. VSV is a minus-strand RNA virus that can infect insects and mammals.

In a second embodiment, the invention relates to a recombinant vesicular stomatitis virus (VSV) vector encoding a modified form of VSV G, wherein the modified form of VSV G may harbor epitopes from the HIV Env membrane proximal external region (MPER). The MPER sequence may be inserted into the membrane proximal region or other domains of VSV G. The G-MPER protein may bind with high avidity to 2F5, 4E10 or other monoclonal antibodies.

In a third embodiment, the invention relates to a recombinant vesicular stomatitis virus (VSV) vector encoding a an N-terminally truncated form of VSV G (G/Stem), wherein the G/Stem may display Env epitope sequences on the surface of VSV particles. The G/Stem may contain a cytoplasmic tail (CT) and trans-membrane (TM) spanning domains of G, a 16- to 68-amino acid membrane proximal extracellular polypeptide (the Stem), wherein HIV Env epitopes are appended to or inserted into the Stem. The HIV Env epitopes may be derived from the gp41 MPER or other regions of Env. The G/Stem-HIV Env epitope molecules may bind to 2F5, 4E10 or other monoclonal antibodies with high affinity.

In a fourth embodiment, the invention relates to a method of generating novel chimeric HIV Env-VSV G (EnvG) molecules expressed and incorporated into VSV which may comprise:
(a) serially passaging replication-competent chimeric VSV-HIV viruses that lack the capacity to encode wild-type G and are dependent on Env or chimeric EnvG molecules for infection and propagation on cells to promote emergence of viruses with greater replicative fitness and
(b) identifying novel mutations that enhance Env or EnvG function in VSV-HIV viruses.

The cells may be CD4/CCR5$^+$ cells. The novel mutations may escalate trimer abundance on the virus particle and/or increase the stability of the functional trimeric form of Env or EnvG. The method may further comprise determining whether the Env or EnvG immunogens elicit broadly neutralizing anti-Env antibodies.

In a fifth embodiment, the invention relates to method of applying selective pressure to generate novel Env, EnvG, or G/Stem-antigen chimeras molecules expressed and incorporated into VSV, wherein the selective pressure may be binding to an antibody of interest, thereby enriching for molecules that may be more immunogenic. The antibody may be 2F5, 4E10, or other Env-specific antibodies.

The present invention also encompasses methods of producing or eliciting an immune response which may comprise administering to a mammal any one of the herein disclosed recombinant VSV vectors.

The present invention also encompasses other plus and minus strand viruses which can be used as recombinant viral vectors in the method of the invention. Such viruses include but are not limited to: Measles virus, Canine distemper virus, Parainfluenza viruses, Sendai virus, Newcastle disease virus, Venezuelan equine encephalitis virus, Sindbis virus, Semliki Forrest virus etc.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in 6 U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIGS. 1A and 1B depict the HIV-1 envelope protein. A. Illustration of the gp160 precursor, which is post-translationally cleaved into the gp120 and gp41 subunits. The locations of the signal and fusion peptides, the Membrane-Proximal External Region (MPER) and the transmembrane (TM) segment are indicated. The ruler denotes amino acid numbering. B. Broadly neutralizing antibodies directed against Env: PG9 and PG16 interacts with conserved residues in the V2 and V3 loops and present an accessible target on gp120; 2G12 binds to oligosaccharides at the tip of gp120; b12 interacts with the CD4 binding site; 2F5 and 4E10 bind adjacent linear epitopes in the gp41 MPER.

FIG. 3 depicts the VSV glycoprotein. The model on the left side is the soluble G ectodomain solved by Roche et al (Roche et al., Science 2007 315, 843-848), which is composed of a number of structural elements including an elongated (β-sheet that contains the fusion peptide. In the middle portion of the Figure, a graphic approximation (in pink) of amino acid residues not included in the crystal structure was inserted, which includes the cytoplasmic tail (CT), the transmembrane (TM) domain, and the short membrane-proximal ectodomain (Stem). Three epitope insertion points were used for preliminary studies: an α-helix at the tip (T), a loop (L) on the side, and a region in the Stem (S). The Stem, together with the TM and CT domains, but without the remainder of the ectodomain, forms the G-Stem polypeptide, which is drawn at the right side of the Figure. The G-Stem protein can be incorporated into virions and can be used as a presentation platform for foreign epitopes.

FIG. 4 depicts HIV Env Immunogens presented on the VSV vector platform. The different chimeric envelope proteins are illustrated from top to bottom: i) the native VSV G trimer, ii) a G trimer with the gp41 MPER inserted into the stem region of G; iii) the G/Stem displaying MPER epitopes; and iv) the Env ectodomain including the MPER, which is incorporated into the VSV particle via the transmembrane segment and cytoplasmic tail of G.

FIG. 6 depicts HIV-1 Env MPER and VSV G stem sequence alignment and insertion/substitution strategies. Top, The MPER of HIV-1 gp41 (SEQ ID NO: 1) (JRFL strain) and the Stem region of VSV G (SEQ ID NO: 2) (Indiana strain) share sequence similarities, which guided the selection of insertion or substitution points in the Stem region for the 2F5 and 4E10 epitopes. The transmembrane domains and the first two residues of the cytoplasmic tails are depicted on the right. Hydrophobic residues are shown in blue. Middle, Generation of the VSV G-2F5-Ins construct (SEQ ID NO: 5) by insertion of the 2F5 epitope (SEQ ID NO: 3) into the G stem region (SEQ ID NO: 4). Flanking linker residues are shown in green. Bottom, Substitution of residues in the G stem region (SEQ ID NOS: 7 and 10 respectively) with the 2F5 (SEQ ID NO: 6) and/or 4E10 (SEQ ID NO: 9) epitopes, resulting in the VSV G-2F5-Sub (SEQ ID NO: 8), VSV G-4E10-Sub (SEQ ID NO: 11), and VSV G-2F5-4E10-Sub (SEQ ID NO: 12) constructs. Sequences similarities between HIV gp41 and VSV G are shown in red.

FIG. 7 depicts insertion points for the 2F5 and 4E10 epitopes in the context of full-length VSV G. The leader peptide, ectodomain, Stem, TM and CT of VSV G are illustrated. The arrow denotes insertion of the 2F5 epitope, while the orange and blue boxes indicate substitution of the 2F5 and 4E10 epitopes, respectively.

FIG. 8 depicts the expression and antibody detection of the VSV G constructs. Western blot using VSV-G, 2F5 and 4E10 antibodies to detect the G protein in lysates from 293T cells transfected with plasmids coding for unmodified VSV G, VSV G-2F5-Ins, VSV G-2F5-Sub, VSV G-4E10-Sub, or VSV G-2F5-4E10-Sub. Mock denotes a transfection with an "empty" plasmid vector. The antibody used for detection is shown under each panel. Molecular weight standards are indicated on the right of each gel.

FIG. 9 depicts the trimerization of the VSV G constructs. Western blot using VSV-G antibody to detect oligomeric G protein on the surface of 293T cells transfected with VSV G constructs, followed by incubation with the chemical cross-linker 3,3'-Dithiobis-[sulfosuccinimidylpropionate] (DTSSP) at various concentrations as indicated above each lane. Monomeric, dimeric and trimeric VSV G forms are detected.

FIG. 11 depicts cell-cell fusion mediated by VSV G. 293T cells transfected with VSV G constructs were exposed briefly to a medium with pH 5.2. After 6-8 hours, formation of syncitia was monitored using a light microscope. The inset in the panel for VSV G-2F5-4E10 at the bottom right shows a small syncitium, which occurs rarely for this construct.

FIG. 13 depicts infectivity of lentiviral particles pseudotyped with VSV G constructs. GFP reporter lentiviruses pseudotyped with VSV G variants were generated in 293T cells and used subsequently to infect naive 293T cells. GFP expression was monitored 72 hours post-infection.

FIG. 15 depicts neutralization of lentiviral particles pseudotyped with VSV G constructs with the 2F5 or 4E10 antibodies. Luciferase reporter lentiviruses pseudotyped with VSV G, VSV G-2F5-Sub or VSV G-4E10-Sub were incubated with various concentrations of 2F5 (left panel) or 4E10 antibody (right panel) prior to infection of naïve cells. Luciferase expression was quantified 48 hours post-infection.

FIG. 16 depicts growth curves of recombinant VSV in Vero cells. Recombinant VSV (rVSV) containing the gene for wild-type G, G-2F5-Sub, G-4E10-Sub or G-2F5-4E10-Sub rescued in 293T cells was used to infect Vero cells at a multiplicity of infection (m.o.i.) of 5. Aliquots of the supernatant were taken at various times post-infection. Subsequently, naïve Vero cells were infected with the samples, followed by a standard plaque assay to determine the viral titer for each time point.

FIG. 17 depicts neutralization of recombinant VSV with 2F5 and 4E10 antibodies. Recombinant VSV containing wild-type G, G-2F5-Sub, G-4E10-Sub or G-2F5-4E10-Sub was incubated with various concentrations of the broadly neutralizing monoclonal antibodies VI-10 (which reacts with the ectodomain of G), 2F5 or 4E10 before addition to naive Vero cells. A standard plaque assay was used to determine the extent of neutralization for each antibody and concentration.

FIGS. 19A-19C depict a schematic illustrating the membrane topology of G and G-Stem proteins. A. Topology of the full-length G protein with the extracellular region, the stem, the transmembrane segment, and the cytoplasmic tail. Four different G-Stem constructs were generated: no stem, short stem, middle stem, and long stem. B. The gp41 MPER was fused to the four G-Stem constructs (GS-MPER fusions). C. Amino acid sequence of the G-Stem (SEQ ID NO: 13). The starting position for each GS variant (no, short, medium, long) is shown. The N-terminal signal sequence is shown in purple, whereas the transmembrane segment is colored red.

FIG. 20 depicts VSV Vector Design. The gene encoding G-Stem variants was inserted into the VSV genome upstream of the N protein near the 3' end. In addition, the full-length G protein is present in the genome. Upon expression, both the G-Stem and full-length G will be incorporated into virus particles as illustrated below the vector genome map.

FIGS. 21A-21D depict analysis of G-Stem-MPER Expression. A. Western Blot analysis of rVSV containing the G-Stem-MPER variants (rVSV-GS-MPER) from the supernatant of infected cells using an anti-VSV-G antibody that reacts with the cyoplasmic tail. LS, long stem; MS, medium stem; SS, short stem; NS, no stem. B. Western Blot analysis of rVSV-GS-MPER from infected cells using an anti-VSV-G antibody. C. Western Blot analysis of rVSV-GS-MPER with the 2F5 antibody. D. Western Blot analysis of rVSV-GS-MPER with the 4E10 antibody.

FIG. 25 depicts rabbit immunogenicity testing. Vaccination and blood collection schedules are listed along a timeline (M, months; W, weeks) at the top. Analysis of antibody reactivity is illustrated in the flow diagram at the left side. The chart on the right side outlines a typical rabbit study.

FIGS. 27A-27B depicts the plasmid sequence of pCINeo-VSV-G (SEQ ID NO: 14) that encodes the G protein from the vesicular stomatitis Indiana virus. Applicants have optimized the gene sequence.

FIGS. 28A-28B depicts the unique XhoI and NotI sites (highlighted) added to the 5' and 3' termini respectively of the VSV G coding sequence (SEQ ID NO: 15) as per the Optimization Strategy detailed in Example 5.

DETAILED DESCRIPTION

Figure 2:
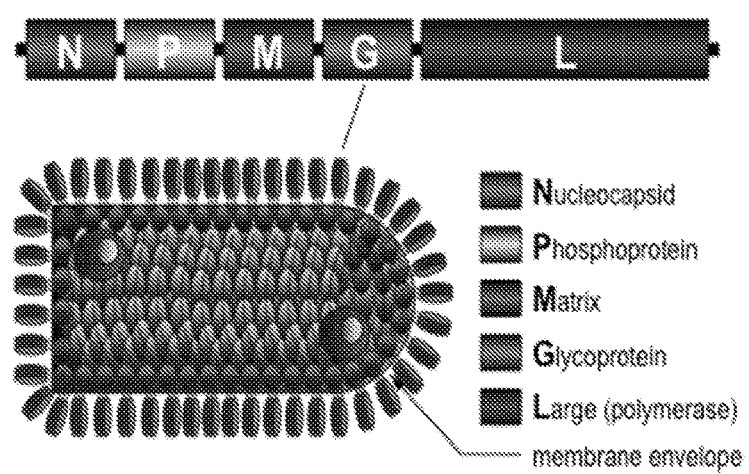
FIG. 2 depicts vesicular stomatitis virus. The negative-sense RNA genome (schematically depicted at the top) encodes five genes in the order 3'-N-P-M-G-L-5'. The surface of the virus particle (bottom) is decorated with approximately 1,200 copies of the glycoprotein (G), which is arranged as trimers. The matrix protein (M) lines the inner surface of the virus particle between the membrane and the nucleocapsid, probably making contact with G as well as the nucleocapsid (N) protein and giving the virus particles their characteristic rod- or bullet-shaped morphology. The polymerase (L) and phosphoprotein (P) are subunits of the RNA-dependent RNA polymerase complex.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, F(ab')$_2$, Fv and scFv which are capable of binding the epitope determinant. These antibody fragments retain some ability to selectively bind with its antigen or receptor and include, for example:
  (i) Fab, the fragment which contains a monovalent antigen-binding fragment of an antibody molecule can be produced by digestion of whole antibody with the enzyme papain to yield an intact light chain and a portion of one heavy chain;
  (ii) Fab', the fragment of an antibody molecule can be obtained by treating whole antibody with pepsin, followed by reduction, to yield an intact light chain and a portion of the 20 heavy chain; two Fab' fragments are obtained per antibody molecule;
  (iii) F(ab')$_2$, the fragment of the antibody that can be obtained by treating whole antibody with the enzyme pepsin without subsequent reduction; F(ab')$_2$ is a dimer of two Fab' fragments held together by two disulfide bonds;
  (iv) scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

It should be understood that the proteins, including the antibodies and/or antigens of the invention may differ from the exact sequences illustrated and described herein. Thus, the invention contemplates deletions, additions and substitutions to the sequences shown, so long as the sequences function in accordance with the methods of the invention. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the Gag, Pol, Env, Nef, RT, and Int sequences of the invention may be altered in these ways.

As regards codon optimization, the nucleic acid molecules of the invention have a nucleotide sequence that encodes the antigens of the invention and can be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens can be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Geneart (geneart.com). Thus, the nucleotide sequences of the invention can readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp:// blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and antibodies and/or antigens of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antibodies and/or antigens of the present invention may be used in accordance with the present invention. In certain embodiments, the antigens and/or antibodies of the present invention may be used in vitro (such as using cell-free expression systems) and/or in cultured cells grown in vitro in order to produce the encoded HIV-antigens and/or antibodies which may then be used for various applications such as in the production of proteinaceous vaccines. For such applications, any vector that allows expression of the antigens and/or antibodies in vitro and/or in cultured cells may be used.

For applications where it is desired that the antibodies and/or antigens be expressed in vivo, for example when the transgenes of the invention are used in DNA or DNA-containing vaccines, any vector that allows for the expression of the antibodies and/or antigens of the present invention and is safe for use in vivo may be used. In preferred embodiments the vectors used are safe for use in humans, mammals and/or laboratory animals.

For the antibodies and/or antigens of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The present invention relates to a recombinant vesicular stomatitis virus (VSV) vector expressing a foreign epitope. Advantageously, the epitope is an HIV epitope. Any HIV epitope may be expressed in a VSV vector. Advantageously, the HIV epitope is an HIV antigen, HIV epitope or an HIV immunogen, such as, but not limited to, the HIV antigens, HIV epitopes or HIV immunogens of U.S. Pat. Nos. 7,341, 731; 7,335,364; 7,329,807; 7,323,553; 7,320,859; 7,311, 920; 7,306,798; 7,285,646; 7,285,289; 7,285,271; 7,282, 364; 7,273,695; 7,270,997; 7,262,270; 7,244,819; 7,244, 575; 7,232,567; 7,232,566; 7,223,844; 7,223,739; 7,223, 534; 7,223,368; 7,220,554; 7,214,530; 7,211,659; 7,211, 432; 7,205,159; 7,198,934; 7,195,768; 7,192,555; 7,189, 826; 7,189,522; 7,186,507; 7,179,645; 7,175,843; 7,172, 761; 7,169,550; 7,157,083; 7,153,509; 7,147,862; 7,141, 550; 7,129,219; 7,122,188; 7,118,859; 7,118,855; 7,118, 751; 7,118,742; 7,105,655; 7,101,552; 7,097,971 7,097,842; 7,094,405; 7,091,049; 7,090,648; 7,087,377; 7,083,787; 7,070,787; 7,070,781; 7,060,273; 7,056,521; 7,056,519; 7,049,136; 7,048,929; 7,033,593; 7,030,094; 7,022,326; 7,009,037; 7,008,622; 7,001,759; 6,997,863; 6,995,008; 6,979,535; 6,974,574; 6,972,126; 6,969,609; 6,964,769; 6,964,762; 6,958,158; 6,956,059; 6,953,689; 6,951,648; 6,946,075; 6,927,031; 6,919,319; 6,919,318; 6,919,077; 6,913,752; 6,911,315; 6,908,617; 6,908,612; 6,902,743; 6,900,010; 6,893,869; 6,884,785; 6,884,435; 6,875,435; 6,867,005; 6,861,234; 6,855,539; 6,841,381 6,841,345; 6,838,477; 6,821,955; 6,818,392; 6,818,222; 6,815,217; 6,815,201; 6,812,026; 6,812,025; 6,812,024; 6,808,923; 6,806,055; 6,803,231; 6,800,613; 6,800,288; 6,797,811; 6,780,967; 6,780,598; 6,773,920; 6,764,682; 6,761,893; 6,753,015; 6,750,005; 6,737,239; 6,737,067; 6,730,304; 6,720,310; 6,716,823; 6,713,301; 6,713,070; 6,706,859; 6,699,722; 6,699,656; 6,696,291; 6,692,745; 6,670,181; 6,670,115; 6,664,406; 6,657,055; 6,657,050; 6,656,471; 6,653,066; 6,649,409; 6,649,372; 6,645,732; 6,641,816; 6,635,469; 6,613,530; 6,605,427; 6,602,709 6,602,705; 6,600,023; 6,596,477; 6,596,172; 6,593,103; 6,593,079;

6,579,673; 6,576,758; 6,573,245; 6,573,040; 6,569,418; 6,569,340; 6,562,800; 6,558,961; 6,551,828; 6,551,824; 6,548,275; 6,544,780; 6,544,752; 6,544,728; 6,534,482; 6,534,312; 6,534,064; 6,531,572; 6,531,313; 6,525,179; 6,525,028; 6,524,582; 6,521,449; 6,518,030; 6,518,015; 6,514,691; 6,514,503; 6,511,845; 6,511,812; 6,511,801; 6,509,313; 6,506,384; 6,503,882; 6,495,676; 6,495,526; 6,495,347; 6,492,123; 6,489,131; 6,489,129; 6,482,614; 6,479,286; 6,479,284; 6,465,634; 6,461,615 6,458,560; 6,458,527; 6,458,370; 6,451,601; 6,451,592; 6,451,323; 6,436,407; 6,432,633; 6,428,970; 6,428,952; 6,428,790; 6,420,139; 6,416,997; 6,410,318; 6,410,028; 6,410,014; 6,407,221; 6,406,710; 6,403,092; 6,399,295; 6,392,013; 6,391,657; 6,384,198; 6,380,170; 6,376,170; 6,372,426; 6,365,187; 6,358,739; 6,355,248; 6,355,247; 6,348,450; 6,342,372; 6,342,228; 6,338,952; 6,337,179; 6,335,183; 6,335,017; 6,331,404; 6,329,202; 6,329,173; 6,328,976; 6,322,964; 6,319,666; 6,319,665; 6,319,500; 6,319,494; 6,316,205; 6,316,003; 6,309,633; 6,306,625 6,296,807; 6,294,322; 6,291,239; 6,291,157; 6,287,568; 6,284,456; 6,284,194; 6,274,337; 6,270,956; 6,270,769; 6,268,484; 6,265,562; 6,265,149; 6,262,029; 6,261,762; 6,261,571; 6,261,569; 6,258,599; 6,258,358; 6,248,332; 6,245,331; 6,242,461; 6,241,986; 6,235,526; 6,235,466; 6,232,120; 6,228,361; 6,221,579; 6,214,862; 6,214,804; 6,210,963; 6,210,873; 6,207,185; 6,203,974; 6,197,755; 6,197,531; 6,197,496; 6,194,142; 6,190,871; 6,190,666; 6,168,923; 6,156,302; 6,153,408; 6,153,393; 6,153,392; 6,153,378; 6,153,377; 6,146,635; 6,146,614; 6,143,876 6,140,059; 6,140,043; 6,139,746; 6,132,992; 6,124,306; 6,124,132; 6,121,006; 6,120,990; 6,114,507; 6,114,143; 6,110,466; 6,107,020; 6,103,521; 6,100,234; 6,099,848; 6,099,847; 6,096,291; 6,093,405; 6,090,392; 6,087,476; 6,083,903; 6,080,846; 6,080,725; 6,074,650; 6,074,646; 6,070,126; 6,063,905; 6,063,564; 6,060,256; 6,060,064; 6,048,530; 6,045,788; 6,043,347; 6,043,248; 6,042,831; 6,037,165; 6,033,672; 6,030,772; 6,030,770; 6,030,618; 6,025,141; 6,025,125; 6,020,468; 6,019,979; 6,017,543; 6,017,537; 6,015,694; 6,015,661; 6,013,484; 6,013,432 6,007,838; 6,004,811; 6,004,807; 6,004,763; 5,998,132; 5,993,819; 5,989,806; 5,985,926; 5,985,641; 5,985,545; 5,981,537; 5,981,505; 5,981,170; 5,976,551; 5,972,339; 5,965,371; 5,962,428; 5,962,318; 5,961,979; 5,961,970; 5,958,765; 5,958,422; 5,955,647; 5,955,342; 5,951,986; 5,951,975; 5,942,237; 5,939,277; 5,939,074; 5,935,580; 5,928,930; 5,928,913; 5,928,644; 5,928,642; 5,925,513; 5,922,550; 5,922,325; 5,919,458; 5,916,806; 5,916,563; 5,914,395; 5,914,109; 5,912,338; 5,912,176; 5,912,170; 5,906,936; 5,895,650; 5,891,623; 5,888,726; 5,885,580 5,885,578; 5,879,685; 5,876,731; 5,876,716; 5,874,226; 5,872,012; 5,871,747; 5,869,058; 5,866,694; 5,866,341; 5,866,320; 5,866,319; 5,866,137; 5,861,290; 5,858,740; 5,858,647; 5,858,646; 5,858,369; 5,858,368; 5,858,366; 5,856,185; 5,854,400; 5,853,736; 5,853,725; 5,853,724; 5,852,186; 5,851,829; 5,851,529; 5,849,475; 5,849,288; 5,843,728; 5,843,723; 5,843,640; 5,843,635; 5,840,480; 5,837,510; 5,837,250; 5,837,242; 5,834,599; 5,834,441; 5,834,429; 5,834,256; 5,830,876; 5,830,641; 5,830,475; 5,830,458; 5,830,457; 5,827,749; 5,827,723; 5,824,497 5,824,304; 5,821,047; 5,817,767; 5,817,754; 5,817,637; 5,817,470; 5,817,318; 5,814,482; 5,807,707; 5,804,604; 5,804,371; 5,800,822; 5,795,955; 5,795,743; 5,795,572; 5,789,388; 5,780,279; 5,780,038; 5,776,703; 5,773,260; 5,770,572; 5,766,844; 5,766,842; 5,766,625; 5,763,574; 5,763,190; 5,762,965; 5,759,769; 5,756,666; 5,753,258; 5,750,373; 5,747,641; 5,747,526; 5,747,028; 5,736,320; 5,736,146; 5,733,760; 5,731,189; 5,728,385; 5,721,095; 5,716,826; 5,716,637; 5,716,613; 5,714,374; 5,709,879; 5,709,860; 5,709,843; 5,705,331; 5,703,057; 5,702,707 5,698,178; 5,688,914; 5,686,078; 5,681,831; 5,679,784; 5,674,984; 5,672,472; 5,667,964; 5,667,783; 5,665,536; 5,665,355; 5,660,990; 5,658,745; 5,658,569; 5,643,756; 5,641,624; 5,639,854; 5,639,598; 5,637,677; 5,637,455; 5,633,234; 5,629,153; 5,627,025; 5,622,705; 5,614,413; 5,610,035; 5,607,831; 5,606,026; 5,601,819; 5,597,688; 5,593,972; 5,591,829; 5,591,823; 5,589,466; 5,587,285; 5,585,254; 5,585,250; 5,580,773; 5,580,739; 5,580,563; 5,573,916; 5,571,667; 5,569,468; 5,558,865; 5,556,745; 5,550,052; 5,543,328; 5,541,100; 5,541,057; 5,534,406 5,529,765; 5,523,232; 5,516,895; 5,514,541; 5,510,264; 5,500,161; 5,480,967; 5,480,966; 5,470,701; 5,468,606; 5,462,852; 5,459,127; 5,449,601; 5,447,838; 5,447,837; 5,439,809; 5,439,792; 5,418,136; 5,399,501; 5,397,695; 5,391,479; 5,384,240; 5,374,519; 5,374,518; 5,374,516; 5,364,933; 5,359,046; 5,356,772; 5,354,654; 5,344,755; 5,335,673; 5,332,567; 5,320,940; 5,317,009; 5,312,902; 5,304,466; 5,296,347; 5,286,852, 5,268,265; 5,264,356; 5,264,342; 5,260,308; 5,256,767; 5,256,561; 5,252,556; 5,230,998; 5,230,887; 5,227,159; 5,225,347; 5,221,610; 5,217,861; 5,208,321; 5,206,136; 5,198,346; 5,185,147; 5,178,865; 5,173,400; 5,173,399; 5,166,050; 5,156,951; 5,135,864; 5,122,446; 5,120,662; 5,103,836; 5,100,777; 5,100,662; 5,093,230; 5,077,284; 5,070,010; 5,068,174; 5,066,782; 5,055,391; 5,043,262; 5,039,604; 5,039,522; 5,030,718; 5,030,555; 5,030,449; 5,019,387; 5,013,556; 5,008,183; 5,004,697; 4,997,772; 4,983,529; 4,983,387; 4,965,069; 4,945,082; 4,921,787; 4,918,166; 4,900,548; 4,888,290; 4,886,742; 4,885,235; 4,870,003; 4,869,903; 4,861,707; 4,853,326; 4,839,288; 4,833,072 and 4,795,739.

Advantageously, the HIV epitope may be an Env precursor or gp160 epitope. The Env precursor or gp160 epitope may be recognized by antibodies PG9, PG16, 2G12, b12, 2F5, 4E10, Z13, or other broad potent neutralizing antibodies.

In another embodiment, HIV, or immunogenic fragments thereof, may be utilized as the HIV epitope. For example, the HIV nucleotides of U.S. Pat. Nos. 7,393,949, 7,374,877, 7,306,901, 7,303,754, 7,173,014, 7,122,180, 7,078,516, 7,022,814, 6,974,866, 6,958,211, 6,949,337, 6,946,254, 6,896,900, 6,887,977, 6,870,045, 6,803,187, 6,794,129, 6,773,915, 6,768,004, 6,706,268, 6,696,291, 6,692,955, 6,656,706, 6,649,409, 6,627,442, 6,610,476, 6,602,705, 6,582,920, 6,557,296, 6,531,587, 6,531,137, 6,500,623, 6,448,078, 6,429,306, 6,420,545, 6,410,013, 6,407,077, 6,395,891, 6,355,789, 6,335,158, 6,323,185, 6,316,183, 6,303,293, 6,300,056, 6,277,561, 6,270,975, 6,261,564, 6,225,045, 6,222,024, 6,194,391, 6,194,142, 6,162,631, 6,114,167, 6,114,109, 6,090,392, 6,060,587, 6,057,102, 6,054,565, 6,043,081, 6,037,165, 6,034,233, 6,033,902, 6,030,769, 6,020,123, 6,015,661, 6,010,895, 6,001,555, 5,985,661, 5,980,900, 5,972,596, 5,939,538, 5,912,338, 5,869,339, 5,866,701, 5,866,694, 5,866,320, 5,866,137, 5,864,027, 5,861,242, 5,858,785, 5,858,651, 5,849,475, 5,843,638, 5,840,480, 5,821,046, 5,801,056, 5,786,177, 5,786,145, 5,773,247, 5,770,703, 5,756,674, 5,741,706, 5,705,612, 5,693,752, 5,688,637, 5,688,511, 5,684,147, 5,665,577, 5,585,263, 5,578,715, 5,571,712, 5,567,603, 5,554,528, 5,545,726, 5,527,895, 5,527,894, 5,223,423, 5,204,259, 5,144,019, 5,051,496 and 4,942,122 are useful for the present invention.

Any epitope recognized by an HIV antibody may be used in the present invention. For example, the anti-HIV antibodies of U.S. Pat. Nos. 6,949,337, 6,900,010, 6,821,744, 6,768,004, 6,613,743, 6,534,312, 6,511,830, 6,489,131, 6,242,197, 6,114,143, 6,074,646, 6,063,564, 6,060,254, 5,919,457, 5,916,806, 5,871,732, 5,824,304, 5,773,247, 5,736,320, 5,637,455, 5,587,285, 5,514,541, 5,317,009, 4,983,529, 4,886,742, 4,870,003 and 4,795,739 are useful for the present invention. Furthermore, monoclonal anti-HIV antibodies of U.S. Pat. Nos. 7,074,556, 7,074,554, 7,070,787, 7,060,273, 7,045,130, 7,033,593, RE39,057, 7,008,622, 6,984,721, 6,972,126, 6,949,337, 6,946,465, 6,919,077, 6,916,475, 6,911,315, 6,905,680, 6,900,010, 6,825,217, 6,824,975, 6,818,392, 6,815,201, 6,812,026, 6,812,024, 6,797,811, 6,768,004, 6,703,019, 6,689,118, 6,657,050, 6,608,179, 6,600,023, 6,596,497, 6,589,748, 6,569,143, 6,548,275, 6,525,179, 6,524,582, 6,506,384, 6,498,006, 6,489,131, 6,465,173, 6,461,612, 6,458,933, 6,432,633, 6,410,318, 6,406,701, 6,395,275, 6,391,657, 6,391,635, 6,384,198, 6,376,170, 6,372,217, 6,344,545, 6,337,181, 6,329,202, 6,319,665, 6,319,500, 6,316,003, 6,312,931, 6,309,880, 6,296,807, 6,291,239, 6,261,558, 6,248,514, 6,245,331, 6,242,197, 6,241,986, 6,228,361, 6,221,580, 6,190,871, 6,177,253, 6,146,635, 6,146,627, 6,146,614, 6,143,876, 6,132,992, 6,124,132, RE36,866, 6,114,143, 6,103,238, 6,060,254, 6,039,684, 6,030,772, 6,020,468, 6,013,484, 6,008,044, 5,998,132, 5,994,515, 5,993,812, 5,985,545, 5,981,278, 5,958,765, 5,939,277, 5,928,930, 5,922,325, 5,919,457, 5,916,806, 5,914,109, 5,911,989, 5,906,936, 5,889,158, 5,876,716, 5,874,226, 5,872,012, 5,871,732, 5,866,694, 5,854,400, 5,849,583, 5,849,288, 5,840,480, 5,840,305, 5,834,599, 5,831,034, 5,827,723, 5,821,047, 5,817,767, 5,817,458, 5,804,440, 5,795,572, 5,783,670, 5,776,703, 5,773,225, 5,766,944, 5,753,503, 5,750,373, 5,747,641, 5,736,341, 5,731,189, 5,707,814, 5,702,707, 5,698,178, 5,695,927, 5,665,536, 5,658,745, 5,652,138, 5,645,836, 5,635,345, 5,618,922, 5,610,035, 5,607,847, 5,604,092, 5,601,819, 5,597,896, 5,597,688, 5,591,829, 5,558,865, 5,514,541, 5,510,264, 5,478,753, 5,374,518, 5,374,516, 5,344,755, 5,332,567, 5,300,433, 5,296,347, 5,286,852, 5,264,221, 5,260,308, 5,256,561, 5,254,457, 5,230,998, 5,227,159, 5,223,408, 5,217,895, 5,180,660, 5,173,399, 5,169,752, 5,166,050, 5,156,951, 5,140,105, 5,135,864, 5,120,640, 5,108,904, 5,104,790, 5,049,389, 5,030,718, 5,030,555, 5,004,697, 4,983,529, 4,888,290, 4,886,742 and 4,853,326, are also useful for the present invention.

The vectors used in accordance with the present invention should typically be chosen such that they contain a suitable gene regulatory region, such as a promoter or enhancer, such that the antigens and/or antibodies of the invention can be expressed.

For example, when the aim is to express the antibodies and/or antigens of the invention in vitro, or in cultured cells, or in any prokaryotic or eukaryotic system for the purpose of producing the protein(s) encoded by that antibody and/or antigen, then any suitable vector can be used depending on the application. For example, plasmids, viral vectors, bacterial vectors, protozoal vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the antibodies and/or antigens under the identified circumstances.

When the aim is to express the antibodies and/or antigens of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the antibodies and/or antigens of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA; ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and can be used as gene delivery vectors.

The present invention relates to recombinant vesicular stomatitis (VSV) vectors, however, other vectors may be contemplated in other embodiments of the invention such as, but not limited to, prime boost administration comprising administration of a recombinant VSV vector in combination with another recombinant vector expressing one or more HIV epitopes.

VSV is a very practical, safe, and immunogenic vector for conducting animal studies, and an attractive candidate for developing vaccines for use in humans. VSV is a member of the Rhabdoviridae family of enveloped viruses containing a nonsegmented, negative-sense RNA genome. The genome is composed of 5 genes arranged sequentially 3'-N-P-M-G-L-5', each encoding a polypeptide found in mature virions. Notably, the surface glycoprotein G is a transmembrane polypeptide that is present in the viral envelope as a homotrimer, and like Env, it mediates cell attachment and infection.

Figure 22:
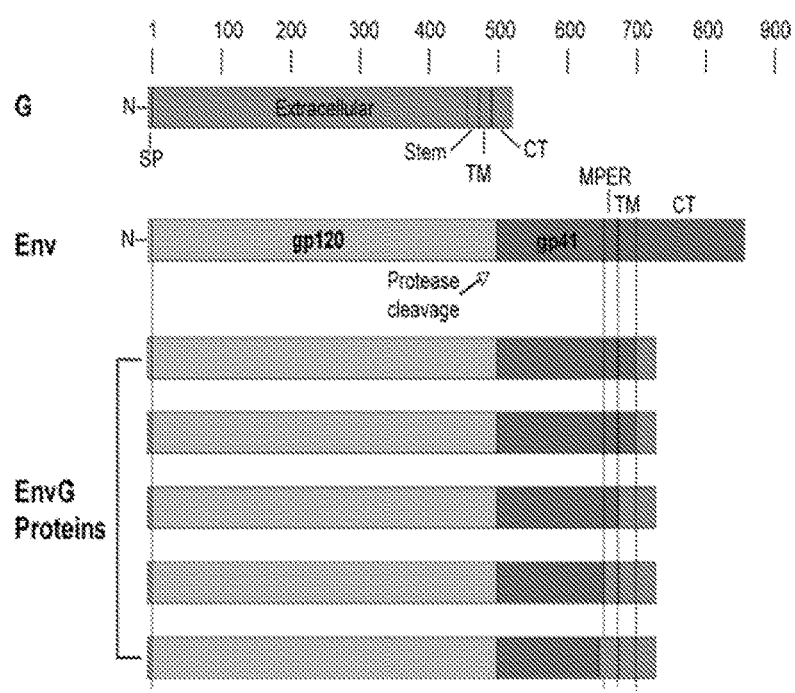
FIG. 22 depicts various VSV G-HIV Env chimeras. The VSV glycoprotein G is shown at the top with features labeled including the signal peptide (SP), the soluble extracellular domain, the Stem, transmembrane (TM) segment and cytoplasmic tail (CT). The HIV-1 Envelope (Env) protein, illustrated below G, is proteolytically processed into the extracellular gp120 and the gp41 domains, the latter containing the MPER, TM segment and CT domains. Various chimeric EnvG proteins are shown at the bottom. Transition points between HIV gp41 and VSV G are be located i) before the CT, ii) before the TM domain, iii) before the MPER, or iv) N-terminal to the complete VSV G-Stem. Translocation of the protein into the lumen of the endoplasmic reticulum can be driven by either the Env or the G signal peptide, although the efficiency and destination vary with the two signals. The ruler at the top denotes the number of amino acid residues.
Figure 23:
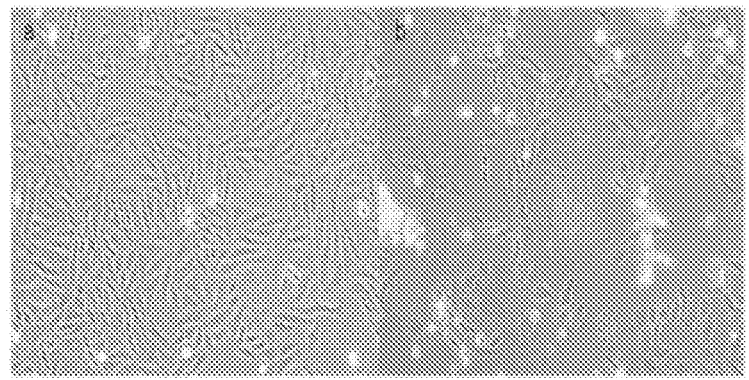
FIG. 23 depicts infectivity of rVSV-EnvG. a, Uninfected GHOST cells (expressing the HIV co-receptors CD4 and CCR5; Cecilia D., et al J. Virol. 1998 September; 7:6988-96) near full confluency. b, GHOST cells infected with rVSV-EnvG virus at 48 hours post-infection. The cytopathic effect (CPE) is clearly visible.

In a first advantageous embodiment, the VSV G is replaced by HIV Env or fragments thereof. The latter will generate chimeric EnvG proteins (see, e.g. FIG. 22).

Figure 5:
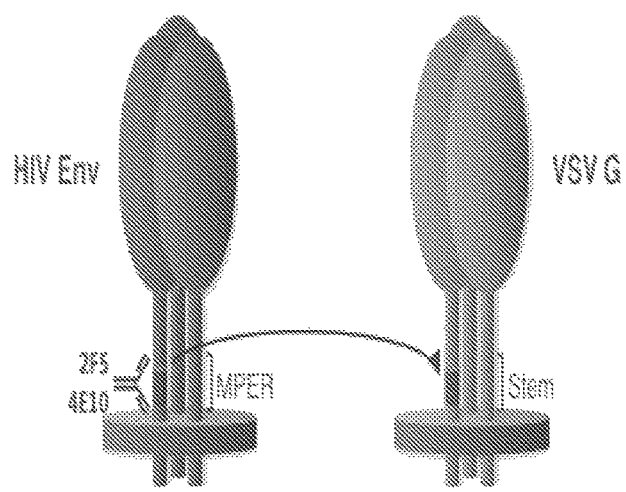
FIG. 5 depicts insertion of the HIV gp41-derived 2F5 and/or 4E10 epitope into the 'stem' region of VSV G, which shares sequence similarities with the gp41 MPER.

In a second advantageous embodiment, VSV G is a carrier or scaffold advantageously for Env MPER epitopes, however, VSV G as a carrier or scaffold may be extended to any foreign epitope (see, e.g., FIGS. 5-7).

Figure 18A:
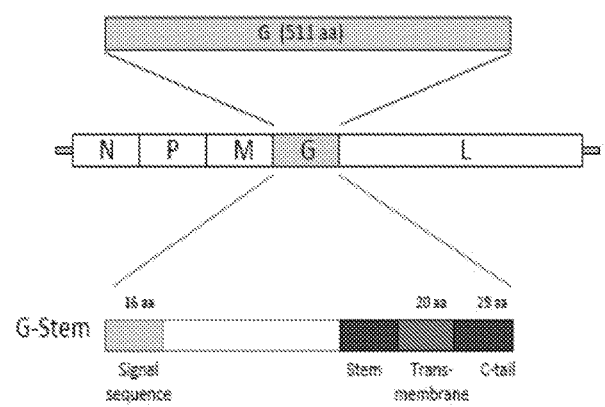
FIGS. 18A and 18B depict a VSV G-Stem platform for expression of fusion proteins. A. Schematic illustration of the VSV genome, the G gene, and the primary structures of the G and G-Stem proteins. B. Foreign gene sequences are fused to the G-Stem via a NheI restriction site, which facilitates incorporation of immunogen coding sequences.
Figure 18B:
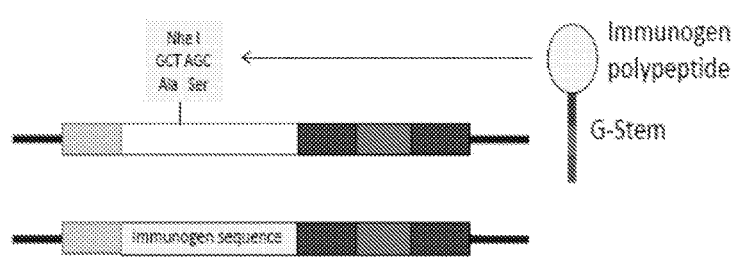

In a third advantageous embodiment, Env MPER epitopes are fused to the VSV G-Stem molecule, however, any foreign epitope may be fused to the VSV G-Stem molecule (see, e.g, FIGS. 18-19).

In a fourth embodiment, the invention pertains to the evolutionary potential of RNA viruses. Such viruses include but are not limited to: VSV, Measles virus, Canine distemper virus, Parainfluenza viruses, Sendai virus, Newcastle disease virus, Venezuelan equine encephalitis virus, Sindbis virus, Semliki Forrest virus etc. Pertaining to the evolutionary potential of VSV, in the first step of EnvG construction, a small panel of genes encoding different forms of EnvG molecules will be produced to determine which motifs from G will optimize expression. Replication-competent 'chimeric' VSV-HIV viruses that lack the capacity to encode wild-type G and are dependent on EnvG for infection and propagation, which are then utilized to direct the evolution of new EnvG molecules that are expressed and incorporated into the virus with greater efficiency.

Figure 24:
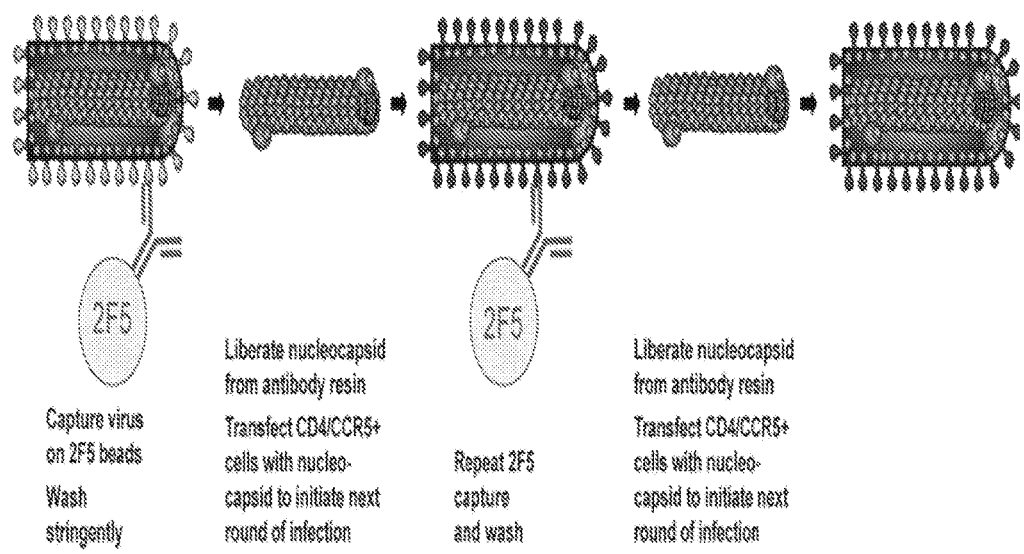
FIG. 24 depicts evolution of Env or EnvG proteins expressed by recombinant VSV. Recombinant VSV encoding a chimeric EnvG molecule are subjected to serial passage and selective pressure. Virus particles that bind with high avidity to 2F5 antibody, for example, are isolated after stringent washing of the antibody beads. Infectious nucleocapsid is liberated from the antibody beads and transfected into CD4/CCR5-positive cells, which initiates a new round of infection. The new generation of recombinant virus undergoes further rounds of selection with increased stringency, which enrich new variants of recombinant viruses that may have improved immunogenic properties.
Figure 26:
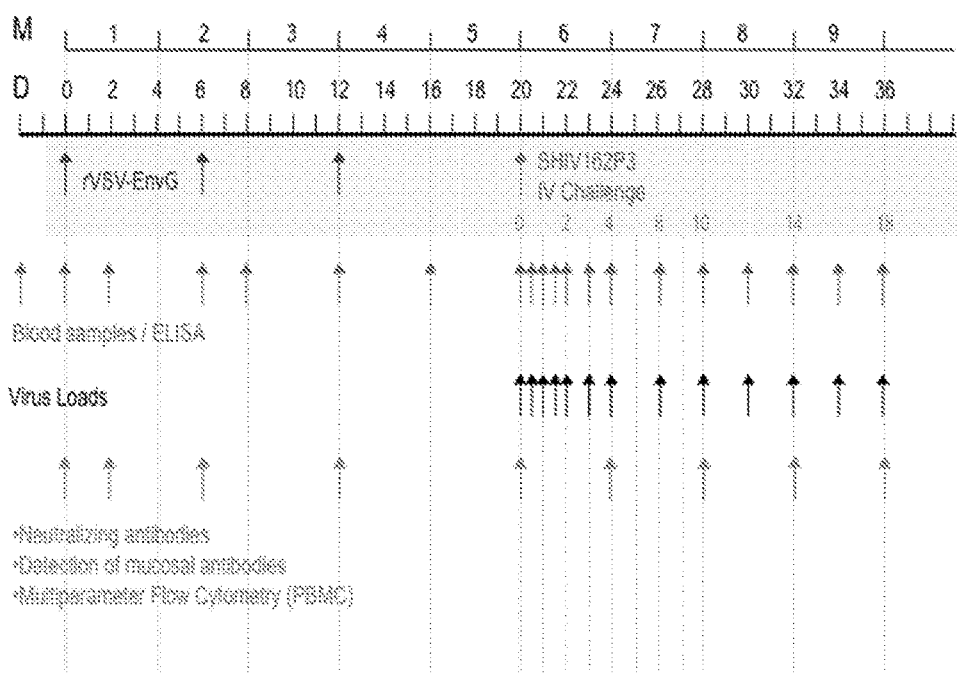
FIG. 26 depicts a plan for vaccination, sampling, and SHIV Challenge. rVSV vaccine candidates are administered 3 times at 6-week intervals after which IV SHIV162P3 challenge is conducted using a challenge stock obtained from the NIH AIDS Research & Reference Reagent Program.

In a fifth embodiment, the invention pertains to application of selective pressure to enrich for molecules that are more immunogenic. The evolution process will occur primarily through nucleotide substitution, followed by selection using a broadly neutralizing antibody against HIV Env, e.g. 2F5 or 4E10, or a broad potent antibody specific for trimeric Env. Due to the nature of negative-strand virus replication, base changes are far more frequent than deletions or insertions, consequently the immunogen will evolve with amino acid substitutions. (see, e.g. FIG. 24)

The VSVs of U.S. Pat. Nos. 7,468,274; 7,419,829; 7,419,674; 7,344,838; 7,332,316; 7,329,807; 7,323,337; 7,259,015; 7,244,818; 7,226,786; 7,211,247; 7,202,079; 7,198,793; 7,198,784; 7,153,510; 7,070,994; 6,969,598; 6,958,226; RE38,824; PP15,957; 6,890,735; 6,887,377; 6,867,326; 6,867,036; 6,858,205; 6,835,568; 6,830,892; 6,818,209; 6,790,641; 6,787,520; 6,743,620; 6,740,764; 6,740,635; 6,740,320; 6,682,907; 6,673,784; 6,673,572; 6,669,936; 6,653,103; 6,607,912; 6,558,923; 6,555,107; 6,533,855; 6,531,123; 6,506,604; 6,500,623; 6,497,873; 6,489,142; 6,410,316; 6,410,313; 6,365,713; 6,348,312; 6,326,487; 6,312,682; 6,303,331; 6,277,633; 6,207,455; 6,200,811; 6,190,650; 6,171,862; 6,143,290; 6,133,027; 6,121,434; 6,103,462; 6,069,134; 6,054,127; 6,034,073; 5,969,211; 5,935,822; 5,888,727; 5,883,081; 5,876,727; 5,858,740; 5,843,723; 5,834,256; 5,817,491; 5,792,604; 5,789,229; 5,773,003; 5,763,406; 5,760,184; 5,750,396; 5,739,018; 5,698,446; 5,686,279; 5,670,354; 5,540,923; 5,512,421; 5,090,194; 4,939,176; 4,738,846; 4,622,292; 4,556,556 and 4,396,628 may be contemplated by the present invention.

The nucleotide sequences and vectors of the invention can be delivered to cells, for example if aim is to express and the HIV-1 antigens in cells in order to produce and isolate the expressed proteins, such as from cells grown in culture. For expressing the antibodies and/or antigens in cells any suitable transfection, transformation, or gene delivery methods can be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies and/or antigens can be carried out in any suitable type of host cells, such as bacterial cells, yeast, insect cells, and mammalian cells. The antibodies and/or antigens of the invention can also be expressed using including in vitro transcription/translation systems. All of such methods are well known by those skilled in the art, and one of skill in the art would readily be able to select a suitable method depending on the nature of the nucleotide sequences, vectors, and cell types used.

In preferred embodiments, the nucleotide sequences, antibodies and/or antigens of the invention are administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. In preferred embodiments the subject is a human, for example a human that is infected with, or is at risk of infection with, HIV-1.

For such in vivo applications the nucleotide sequences, antibodies and/or antigens of the invention are preferably administered as a component of an immunogenic composition comprising the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the antibodies and/or antigens of the invention to a subject, such as a human, such that the antibodies and/or antigens are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

An immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri (caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is commercially available under the name Provax® (IDEC Pharmaceuticals, San Diego, Calif.).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., $AlK(SO_4)_2$, $AlNa(SO_4)_2$, $AlNH(SO_4)_2$, silica, alum, $Al(OH)_3$, $Ca_3(PO_4)_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC31; see Schellack, C. et al (2003) Proceedings of the 34th Annual Meeting of the German Society of Immunology; Lingnau, K. et al (2002) Vaccine 20(29-30): 3498-508), JuvaVax™ (U.S. Pat. No. 6,693,086), certain natural substances (e.g., wax D from *Mycobacterium tuberculosis*, substances found in *Cornyebacterium parvum*, *Bordetella pertussis*, or members of the genus *Brucella*), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689,338; 5,238,944; Zuber, A. K. et al (2004) 22(13-14): 1791-8), and the CCR5 inhibitor CMPD167 (see Veazey, R. S. et al (2003) J. Exp. Med. 198: 1551-1562).

Aluminum hydroxide or phosphate (alum) are commonly used at 0.05 to 0.1% solution in phosphate buffered saline. Other adjuvants that can be used, especially with DNA vaccines, are cholera toxin, especially CTA1-DD/ISCOMs (see Mowat, A. M. et al (2001) J. Immunol. 167(6): 3398-405), polyphosphazenes (Allcock, H. R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-α, IFN-β, and IFN-γ (Boyer et al., (2002) J. Liposome Res. 121:137-142; WO01/095919), immunoregulatory proteins such as CD4OL (ADX40; see, for example, WO03/063899), and the CD1a ligand of natural killer cells (also known as CRONY or α-galactosyl ceramide; see Green, T. D. et al, (2003) J. Virol. 77(3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which can be administered either as proteins or in the form of DNA, on the same expression vectors as those encoding the antigens of the invention or on separate expression vectors.

In an advantageous embodiment, the adjuvants may be lecithin is combined with an acrylic polymer (Adjuplex-LAP), lecithin coated oil droplets in an oil-in-water emulsion (Adjuplex-LE) or lecithin and acrylic polymer in an oil-in-water emulsion (Adjuplex-LAO) (Advanced BioAdjuvants (ABA)).

The immunogenic compositions can be designed to introduce the nucleic acids or expression vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulations can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the nucleic acids and expression vectors of the invention (collectively, the immunogens) in the immunogenic composition of the invention can be readily determined by those of skill in the art. For example, the dosage of the immunogens can vary depending on the route of administration and the size of the subject. Suitable doses can be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of HIV infection, or evidence of HIV infection, or in advance of any symptom due to AIDS, especially in high-risk subjects. The prophylactic administration of the immunogenic compositions can serve to provide protective immunity of a subject against HIV-1 infection or to prevent or attenuate the progression of AIDS in a subject already infected with HIV-1. When provided therapeutically, the immunogenic compositions can serve to ameliorate and treat AIDS symptoms and are advantageously used as soon after infection as possible, preferably before appearance of any symptoms of AIDS but may also be used at (or after) the onset of the disease symptoms.

The immunogenic compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes can be oral, intranasal or by any other suitable route. Delivery also be accomplished via a mucosal surface such as the anal, vaginal or oral mucosa.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens, for example DNA prime-Adenovirus boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

The prime-boost regimen can also include VSV vectors that derive their G protein or G/Stem protein from different serotype vesicular stomatitis viruses (Rose N F, Roberts A, Buonocore L, Rose J K. Glycoprotein exchange vectors based on vesicular stomatitis virus allow effective boosting and generation of neutralizing antibodies to a primary isolate of human immunodeficiency virus type 1. J Virol. 2000 December; 74(23):10903-10). The VSV vectors used in these examples contain a G or G/Stem protein derived from the Indiana serotype of VSV. Vectors can also be constructed to express epitopes in the context of G or G/Stem molecules derived from other VSV serotypes (i.e. vesicular stomatitis New Jersey virus or vesicular stomatitis Alagoas virus) or other vesiculoviruses (i.e. Chandipura virus, Cocal virus, Isfahan virus). Thus an epitope like the HIV MPER can be delivered in a prime in the context of an G or G/Stem molecule that is from the Indiana serotype and the immune system can be boosted with a vector that expresses epitopes in the context of second serotype like New Jersey. This circumvents anti-G immunity elicited by the prime, and helps focus the boost response against the foreign epitope.

A specific embodiment of the invention provides methods of inducing an immune response against HIV in a subject by administering an immunogenic composition of the invention, preferably comprising an adenovirus vector containing DNA encoding one or more of the epitopes of the invention, one or more times to a subject wherein the epitopes are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. In an advantageous embodiment, the other HIV immunogen is env, preferably the HIV env trimer.

Many other HIV immunogens are known in the art, one such preferred immunogen is HIVA (described in WO 01/47955), which can be administered as a protein, on a plasmid (e.g., pTHr.HIVA) or in a viral vector (e.g., MVA-.HIVA). Another such HIV immunogen is RENTA (described in PCT/US2004/037699), which can also be administered as a protein, on a plasmid (e.g., pTHr.RENTA) or in a viral vector (e.g., MVA.RENTA).

For example, one method of inducing an immune response against HIV in a human subject comprises administering at least one priming dose of an HIV immunogen and at least one boosting dose of an HIV immunogen, wherein the immunogen in each dose can be the same or different, provided that at least one of the immunogens is an epitope of the present invention, a nucleic acid encoding an epitope of the invention or an expression vector, preferably a VSV vector, encoding an epitope of the invention, and wherein the immunogens are administered in an amount or expressed at a level sufficient to induce an HIV-specific immune response in the subject. The HIV-specific immune response can include an HIV-specific T-cell immune response or an HIV-specific B-cell immune response. Such immunizations can be done at intervals, preferably of at least 2-6 or more weeks.

It is to be understood and expected that variations in the principles of invention as described above may be made by one skilled in the art and it is intended that such modifications, changes, and substitutions are to be included within the scope of the present invention.

The invention will now be further described by way of the following non-limiting examples.

EXAMPLES

Example 1: Insertion of the HIV-1 gp41 Epitopes 2F5 and 4E10 into the Membrane-Proximal Region of the Vesicular Stomatitis Virus Glycoprotein The membrane-proximal external region (MPER) of HIV-1 gp41, which is recognized by the broadly neutralizing monoclonal antibodies 2F5 and 4E10, is an important target for an HIV vaccine. However, efforts to mimic the 2F5 and 4E10 epitopes outside the context 30 of the gp41 MPER have had minimal success so far. In this study, Applicants used the envelope glycoprotein G of Vesicular Stomatitis Virus (VSV) as a scaffold. VSV G, which forms homotrimeric spikes on the viral surface, is responsible for binding of the virus to cells and promotes fusion of the viral and cellular membranes. The "stem" region of VSV G, which lies immediately N-terminal of its single transmembrane segment, shares sequence similarities with the gp41 MPER. Applicants inserted the gp41 sequences corresponding to the 2F5 and 4E10 neutralizing epitopes into the stem region of VSV G and evaluated the function and antibody reactivity of the chimeric polypeptides. VSV-G-2F5 and VSV-G-4E10 formed trimers and were transported to the cell surface, where they were detected by the 2F5 and 4E10 monoclonal antibodies, respectively. Reporter lentiviruses pseudotyped with VSV G-2F5 or VSV-G-4E10 were infectious, and they were efficiently neutralized by the 2F5 or 4E10 monoclonal antibodies. Recombinant VSV containing G-2F5, G-4E10 or G-2F5-4E10 on the viral surface was infectious, replication-competent, and sensitive to neutralization by the 2F5 or 4E10 monoclonal antibodies. Applicants are currently determining if the recombinant VSVs encoding MPER epitopes elicit neutralizing antibodies specific for the HIV gp41 epitopes in a small animal model. Taken together, Applicants' approach represents a novel strategy to develop a vaccine that induces a humoral immune response against HIV.

Example 2: Using VSV Vectors to Display and Evolve Novel HIV Envelope Immunogens The goal of this Example is to design and develop novel HIV-1 envelope protein (Env) immunogens capable of eliciting broadly protective neutralizing antibody responses for use as vaccine candidates. Applicants take advantage of the unique biological properties of vesicular stomatitis virus (VSV) as vaccine delivery vehicle to present and effectively deliver HIV Env immunogens. In addition, Applicants use the high evolutionary potential of VSV to biologically derive unique mutant HIV Envs with enhanced immunogenicity. Novel candidates are used to vaccinate rabbits to determine their capacity to elicit antibodies with enhanced HIV neutralizing activity, and those VSV-vectored vaccines that evoke responses with increased breadth of neutralization are tested in macaques. Applicants achieve these goals by completing the Specific Aims below:

1. Vaccine Platform 1: Optimize HIV Env (derived from $SHIV_{SF162P3}$) for expression as functional stable trimers on the surface of VSV particles, and produce 'chimeric viruses', in which the gene encoding the VSV surface glycoprotein (G) are functionally replaced by HIV Env. Env modifications described below are investigated to identify the optimal form for expressing abundant functional trimers on VSV particles that specifically direct infection of cells expressing the CD4 and CCR5 coreceptors (CD4/CCR5$^+$ cells). Additionally, Applicants take advantage of the innate ability of VSV to rapidly accrue adaptive mutations to further optimize expression of functional Env trimers by subjecting replication-competent VSV-Env chimeric viruses to serial passage on CD4/CCR5$^+$ cell lines to biologically select for Env mutations that improve replicative fitness. Moreover, to develop additional novel Env immunogens, methods to apply selective pressure during serial passage are developed using the broadly neutralizing antibodies against Env (e.g. monoclonal antibodies 2F5, 4E10, 2G12, b12, PG9, PG16 and other antibodies, including broad potent neutralizing trimer-specific antibodies).

2. Vaccine Platform 2: Produce recombinant VSV (rVSV) vectors that encode modified forms of VSV G, which harbor epitopes from the HIV Env membrane proximal external region (MPER). This takes advantage of several G protein properties including: i) it is a glycosylated transmembrane protein abundantly expressed on the VSV particle; ii) it is a potent immunogen; iii) it contains a hydrophobic membrane-proximal region that resembles the Env MPER, and iv) G trimerizes and provides a platform for multimeric configurations of MPER epitopes. Although several domains in G are tested as sites for insertion of MPER sequences, Applicants focus on the membrane proximal region of G, which provides a similar membrane-associated environment for the most authentic presentation of MPER epitopes. Env MPER insertions that do not abolish the function of VSV G are delivered using VSV vectors and advanced into rabbit immunogenicity studies. Additionally, VSV encoding G-MPER hybrids are subjected to serial passage to determine whether virus expressing a fitness advantage emerges with unique mutations that affect the MPER epitope configuration. Moreover, serial passage also are conducted using conditions that select virus expressing G-MPER proteins that bind with high avidity to the 2F5 and 4E10 mAbs to derive unique immunogens.

3. Vaccine Platform 3: An N-terminally truncated form of VSV G (called G/Stem) are used to present Env epitope sequences on the surface of VSV particles. The G/Stem molecule contains the cytoplasmic tail (CT) and transmembrane (TM) spanning domains of G as well as a short 16- to 68-amino acid membrane proximal extracellular polypeptide (the Stem) to which HIV Env epitopes are appended. Several forms of G/Stem, which vary in length and amino acid sequence, are investigated to determine the optimal form for display of MPER epitopes on the surface of VSV particles and the plasma membrane of infected cells. VSV encoding G/Stem fusion proteins can be propagated using G trans-complementation or by generating recombinant virus that contains a functional G gene in addition to the G/Stem coding sequence. Novel G/Stem-MPER molecules are evolved by serial passage under conditions that select for vectors encoding mutant molecules that bind to the 2F5 and 4E10 mAbs with high affinity.

4. In Vivo Studies: After validating their in vitro properties, promising vaccine candidates developed in Aims 1-3 are evaluated by vaccinating rabbits. Enzyme-linked immunosorbent assays (ELISAs) are conducted first to screen for serum antibodies that react with HIV Env, and those immune sera that contain significant titers are evaluated in HIV neutralization assays using virus-like particles pseudotyped with Env from various HIV strains. The top rVSV-Env vaccine candidates that evoke production of broadly neutralizing antibodies in vaccinated rabbits are advanced into nonhuman primate studies. Rhesus macaques are vaccinated to determine whether immunization protects macaques from subsequent intravenous challenge with the SIV-HIV chimeric virus $SHIV_{SF162P3}$, which expresses an HIV envelope protein.

Example 3: Optimization of Immunogen Presentation by G-Stem Vectors

To develop a platform that can be used to display immunogens on the surface of virus particles or infected cells, Applicants have engineered vesicular stomatitis virus (VSV) vectors to encode a truncated form of the viral transmembrane glycoprotein protein (G) that can be modified to express foreign epitopes anchored to virus envelop or cell membrane. The truncated form of G, called G-Stem (FIG. 18A), retains amino acid sequences that are essential for directing insertion of the molecule into the membrane (the signal peptide), anchoring the protein in the viral envelop or cellular lipid bilayer (the transmembrane domain; TM), and promoting incorporation into the budding viral particle (C-terminal domain). Additionally, a small membrane proximal region of the external domain of G (the Stem) is retained in most constructs because it provides a short stalk on which to append epitopes (FIG. 18B), and importantly, sequences in the Stem are known to promote efficient assembly of VSV particles [Robison & Whitt, J Virol 2000; 74:2239-2246].

Because the Stem domain plays at least two significant roles in Applicants' epitope display vectors—it serves as the platform on which epitopes are attached and displayed, and it plays a role in VSV maturation—Applicants anticipated that it might be necessary to empirically determine the optimal Stem sequence needed for expression and membrane incorporation of G-Stem-Epitope fusion proteins. Applicants tested this assumption by constructing 4 different G-Stem fusion proteins that contained the HIV Env membrane proximal external region (MPER) [Montero et al., Microbiol Mol Biol Rev 2008; 72:54-84] fused to Stem domains that were 68, 42, 16 or 0 amino acids in length, referred to as long stem (LS), medium stem (MS), short stem (SS), and no stem (NS), respectively (FIGS. 19A-C).

The 4 G-Stem-MPER (GS-MPER) molecules were expressed using a novel replication-competent VSV vector that retains a functional G protein and expresses the GS-MPER fusion proteins from an added transcription unit inserted in the highly-transcribed promoter proximal position in the viral genome (FIG. 20). Consequently, the MPER expression vectors express GS-MPER fusion proteins as well as wild-type G protein. Expression of native G protein confers a replication-competent phenotype of these recombinant viruses, and importantly, this also means that infected cells will produce wild-type G and GS-MPER proteins and that both proteins can be inserted into cell membrane and viral envelop (right side of FIG. 20B).

After the recombinant VSV-G-Stem-MPER vectors were constructed, they were used to infect Vero cells and assess expression of the GS-MPER fusion proteins and determine their relative abundance in virus particles (FIG. 21). FIG. 21 shows a Western blot that was used to analyze G and G-Stem-MPER proteins found in the medium supernatant of infected cells. The source of G and GS MPER fusion proteins in the supernatant primarily should be virus that has budded out of infected cells; therefore, the proteins visualized in Panel A provide an estimate of the relative G and GS-MPER abundance in progeny virus particles. The blot in Panel A was reacted with antibody that recognizes the C-terminus of VSV G, which is present on both the native G protein the G-Stem-MPER molecules. The results indicate that NS-MPER and SS-MPER are present at higher levels in the virus particle than MS-MPER or LS-MPER, and that none of the G-Stem-MPERs are as abundant as the native G protein. It is important to note that a proteolytic fragment of G comigrates with the NS-MPER at the top of the gel (Lane 6) making it difficult to estimate its abundance. The relative amount of the 4 MPER-containing molecules is more clearly shown in Panels C and D where the GS-MPER proteins are reacted with MPER-Specific monoclonal antibodies 2F5 and 4E10. In Panel C for example, the relative amounts of NS-MPER (Lane 6) and SS-MPER (Lane 5) are clearly greater than MS- and LS-MPER (Lanes 3 and 4) in virus particles found in the supernatant. It is worth noting that the LS-MPER molecule is expressed at relatively high levels in infected cells as shown in Panel B (Lane 2) suggesting that this form of G-Stem-MPER is expressed but not efficiently incorporated into virus particles. The MS-MPER protein is evident in the infected cells (Panel B, Lane 3) but at low levels indicating that it is expressed poorly or it is unstable compared to the other GS-MPERS. Finally, it is notable that the NS-MPER protein, which lacks the Stem completely, seems to be incorporated at the highest levels of all of the G-Stem-MPERs (FIGS. 21C and D, Lanes 5 and 6). This finding seems to be contrary to the known role of Stem in virus particle maturation [Robison & Whitt, J Virol 2000; 74:2239-2246], but it is consistent with Applicants' results that show that the MPER and smaller peptides from the MPER regions can functionally substitute for the Stem (see, e.g. FIG. 14).

Taken together, these results show that achieving significant expression of G-Stem fusion proteins in infected cells and on virus particles requires optimization of the Stem domain. Applicants' finding that the NS Stem domain is perhaps optimal for expression of HIV MPER probably reflects the fact that the MPER has Stem-like properties. Other antigens expressed as G-Stem-antigen fusions may require different lengths of Stem to be incorporated efficiently into cellular or viral membranes.

Example 4: Insertion of the HIV-1 gp41 Epitopes 2F5 and 4E10 into the Membrane Proximal Region of the Vesicular Stomatitis Virus Glycoprotein Broadly neutralizing antibodies against the HIV Env protein may bind epitopes on gp120 and gp41 (see, e.g., FIG. 1B). Such antibodies include, but are not limited to, PG9 and PG16 (which bind the base of V1/V37372 loops and are trimer-specific), 2G12 (which binds carbohydrates), b12 (which binds the CD4-binding site) and 2F5, 4E10 and Z13 (which bind the membrane-proximal external region (MPER)).

A schematic of VSV is presented in FIG. 2. VSV is an enveloped, negative-strand RNA virus of the Rhabdoviridae family. VSV infects human cells, but is not pathogenic and propagates robustly in vitro and is a safe and immunogenic vector for conducting animal studies.

A schematic of the VSV glycoprotein G is presented in FIG. 3. VSV glycoprotein G is a single envelope glycoprotein on the viral surface that forms trimers (ca. 1,200 molecules arranged as 400 trimers). VSV glycoprotein G mediates attachment, fusion, and entry of VSV into host cell, accepts insertion of short amino acid sequences at certain positions and has a membrane-proximal 'stem' region that shares similarities with the MPER of HIV-1 gp41.

Glycoprotein G is envisioned as an insertion site. In particular, epitope sequences, in particular HIV epitope sequences, more preferably HIV gp41 2F5 and 4E10 epitope sequences may be inserted into the stem region of VSV G. Replication-competent, recombinant VSV containing the modified G protein may be generated for use as an immunogen. FIG. 5 presents a schematic of insertion and substitution of HIV gp41 2F5 and 4E10 epitopes. FIG. 6 depicts insertion and substitution of the 2F5 and 4E10 epitopes. For an insertion, the 2F5 epitope and flanking residues was added to the VSV G stem region. For a substitution, residues in the VSV G stem region were replaced by the 2F5 and/or 4E10 epitopes. A summary of the VSV G constructs are presented in FIG. 7. The expression vector was pCI-Neo (deltaT7).

A Western blot demonstrating the expression and antibody recognition of VSV G proteins expressed from plasmid DNA constructs is presented in FIG. 8. VSV constructs were expressed transiently in 293T cells and the Western blot was performed with lysates (2% CHAPS). The Western blot showed that the stem region of VSV G tolerated the insertion of the 2F5 and/or 4E10 epitope, and that modified VSV G constructs were detected by the 2F5 and 4E10 antibodies.

Trimerization of VSV G on the cell surface is presented in FIG. 9. The VSV G plasmid DNA constructs were expressed in 293T cells, chemical crosslinking was performed with DTSSP (3,3'-Dithiobis-[sulfosuccinimidyl-propionate]) on intact cells and western blot with cell lysates was performed. As shown in FIG. 9, all VSV G variants form trimers on the surface of 293T cells.

Figure 10:
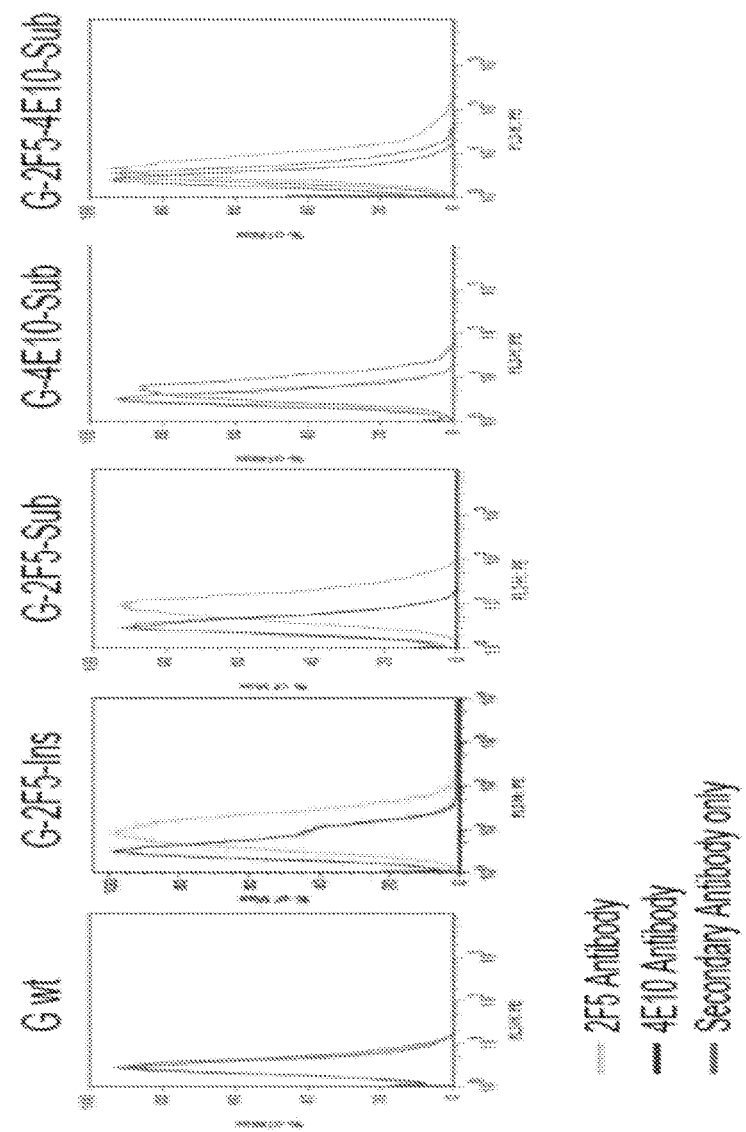
FIG. 10 depicts cell surface expression of VSV G constructs. 293T cells transfected with VSV G constructs were stained with an antibody specific for the ectodomain of VSV G, or with 2F5 or 4E10 antibodies, followed by analysis of the samples by flow cytometry.

Cell surface expression of VSV G constructs is presented in FIG. 10. The VSV G constructs were transiently expressed in 293T cells, and flow cytometry was performed 24 hours post-transfection. The modified VSV G constructs were expressed on the cell surface and detected by the 2F5 and 4E10 antibodies.

VSV G mediated cell-cell fusion is presented in FIG. 11. 293T cells were transfected with plasmid encoding VSV G, briefly exposed to pH 5.2 after 24 hours, and syncitia formation was observed. As shown in FIG. 11, VSV G-2F5-Sub and VSV G-4E10-Sub both induced cell-cell fusion. In addition, VSV G-2F5-4E10-Sub showed small areas of cell-cell fusion in rare cases. It was postulated that the modified G proteins may confer virus entry. To answer this question, a lentivirus reporter system was developed.

Figure 12:
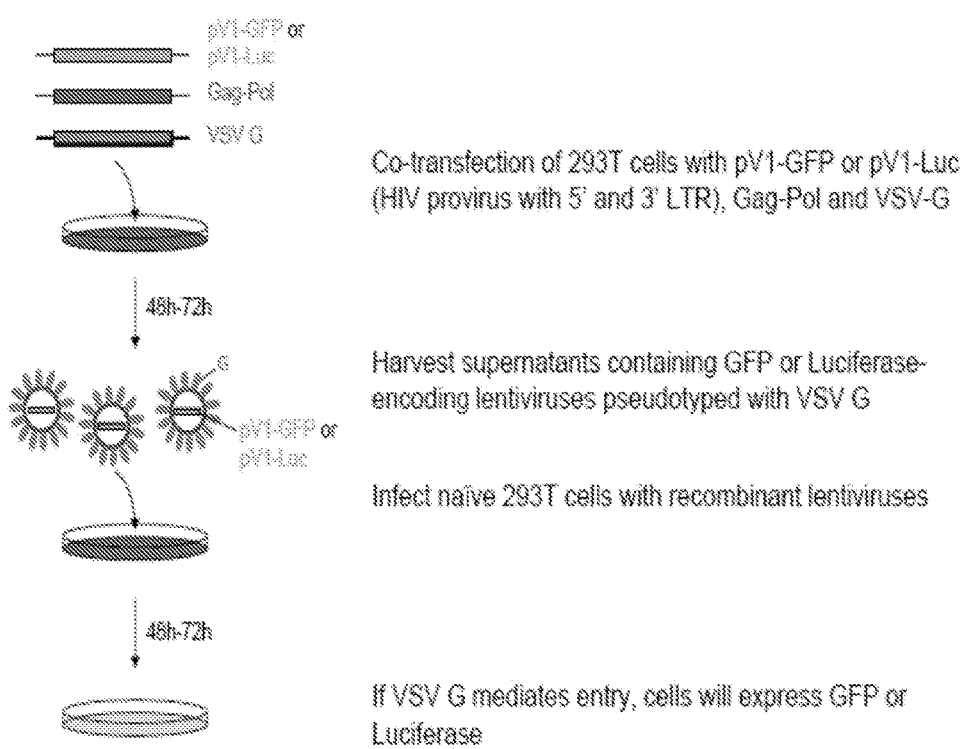
FIG. 12 depicts a reporter assay for functional analysis of modified VSV G proteins. A reporter lentivirus coding for green fluorescent protein (GFP) or luciferase (Luc) was packaged with Gag-Pol and pseudotyped with the VSV G variants and subsequently used to infect naïve 293T cells. GFP or luciferase expression was analyzed 72 hours post-infection.

A lentivirus reporter system is presented in FIG. 12. 293T cells were co-transfected with reporter plasmids pV1-GFP or pV1-Luc (HIV provirus with 5' and 3' LTR), and plasmids coding for Gag-Pol and VSV-G. Supernatants containing GFP or luciferase-encoding lentiviruses pseudotyped with VSV G were harvested, followed by infection of naive 293T cells. If VSV G mediates entry, cells will express GFP or luciferase.

Infectivity of lenviruses pseudotyped with VSV G is presented in FIG. 13. 293T cells were infected with recombinant GFP-lentiviruses pseudotyped with VSV G variants. As shown in FIG. 13, the infectivity of VSV G-2F5-Sub and VSV G-4E10-Sub was similar to wild-type G.

Figure 14:
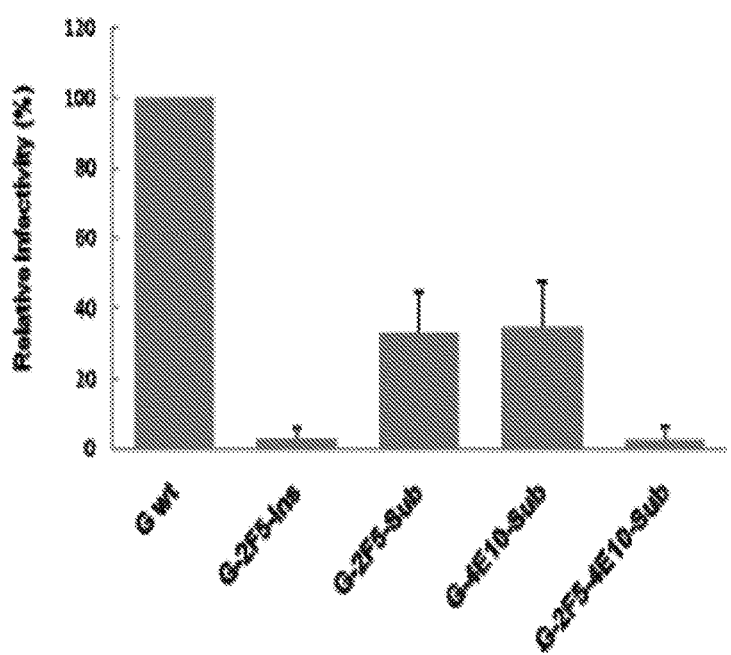
FIG. 14 depicts quantification of infectivity of lentiviral particles pseudotyped with VSV G constructs. Naïve 293T cells were infected with luciferase reporter lentiviruses pseudotyped with VSV G variants, followed by quantification of luciferase expression 48 hours post-infection.

Infectivity of reporter lentiviruses pseudotyped with VSV G is presented in FIG. 14. 293T cells were infected with recombinant Luc-lentiviruses pseudotyped with VSV G variants. Lentiviruses pseudotyped with VSV G-2F5-Sub and VSV G-4E10-Sub retained 33% and 35% of infectivity compared to wild-type VSV G. It was postulated that these viruses be neutralized with the 2F5 and 4E10 antibodies.

Neutralization of lentiviruses pseudotyped with VSV G is depicted in FIG. 15. Luc-lentiviruses pseudotyped with VSV G-2F5-Sub or VSV G-4E10-Sub were incubated with 2F5 or 4E10 antibody at various concentrations. Subsequently, 293T cells were infected with the Luc-lentiviruses, followed by assaying luciferase activity at 3 days post-infection. Luc-lentiviruses pseudotyped with VSV G-2F5-Sub and VSV G-4E10-Sub were efficiently neutralized with the 2F5 and 4E10 antibody, respectively. It was then postulated that modified G proteins could be incorporated into recombinant VSV.

Recombinant VSV containing the gene coding for G-2F5-Sub, G-4E10-Sub and G-2F5-4E10-Sub were rescued. A growth curve analysis by plaque assay on Vero cells (m.o.i of 5) is shown in FIG. 16. The growth kinetics of rVSV containing G-2F5-Sub, G-4E10-Sub or G-2F5-4E10-Sub were similar to wild-type. It was then postulated that rVSV G-2F5-Sub, rVSV G-4E10-Sub and rVSV G-2F5-4E10-Sub could be neutralized with the 2F5 and 4E10 antibodies.

Neutralization of recombinant VSV with various antibodies is shown in FIG. 17. 5000 pfu rVSV G-2F5-Sub, rVSV G-4E10-Sub or rVSV G-2F5-4E10-Sub were incubated with VI-10 (control antibody against the ectodomain of VSV G, i.e. it should neutralize all viruses with G), 2F5 or 4E10 at various concentrations, followed by a plaque assay on Vero cells. As shown in FIG. 17, rVSV containing G-2F5-Sub, G-4E10-Sub or G-2F5-4E10-Sub was efficiently neutralized by the 2F5 and/or 4E10 antibodies.

To summarize this Example: (1) the 'stem' region of the Vesicular Stomatitis Virus (VSV) glycoprotein tolerated the insertion of the HIV-1 gp41 2F5 and 4E10 epitope sequences, (2) the modified VSV G proteins were expressed on the cell surface and detected by the respective HIV broadly neutralizing antibodies, (3) lentiviruses pseudotyped with VSV G-2F5-Sub or VSV G-4E10-Sub were infectious and could be neutralized with the 2F5 and 4E10 antibody, respectively and (4) recombinant VSVs with G-2F5-Sub, G-4E10-Sub or G-2F5-4E10-Sub were infectious, had similar growth kinetics like wild-type rVSV, and could be efficiently neutralized with the 2F5 and 4E10 antibodies. Applicants conclude that the HIV-1 gp41 2F5 and 4E10 epitope sequences were presented in a native-like conformation in the 'stem' region of the VSV glycoprotein.

Example 5: Optimization Strategy Adopted for Optimization of VSV G Protein Coding Sequence The gene was optimized for expression in eukaryotic cells using the following steps:
1. Started with amino acid sequence for VSV G serotype Indiana, strain Orsay (Genbank M11048.1)
2. The amino acid sequence was reverse-translated using the OPTIMIZER webtool (available on the OPTIMIZER website associated with Universitat Rovira i Virgili (URV)) and a human codon frequency table [Puigbò P et al. Nucleic Acids Res. 2007 July; 35 (Web Server issue):W126-31]

3. The DNA sequence obtained from reverse-translation was scanned for potential mRNA splice donor and acceptor sequences using the Splice Site Prediction webtool available on the fruitfly.org website [Reese M G et al. J Comput Biol. 1997 Fall; 4(3):311-23]. Potential splicing signals were disrupted subsequently by introducing one or two synonymous codons, which altered key elements in the donor or acceptor site. Synonymous codons were selected based on frequencies found in the Codon Table published by Zhang et al [Hum Mol Genet. 1998 May; 7 (5):919-32] for GC-rich transcripts.

4. The reverse-translated sequence also was scanned for homopolymeric sequences≥5 nucleotides. Those that were ≥5 were interrupted by substitution of sequence with a synonymous codon as described in the step above.

5. The sequence was scanned for the presence of mRNA instability elements [Zubiaga A M et al. 1995, Mol. Cell. Biol. 15: 2219-2230]. None were found.

6. Optimal translation initiation (Kozak element [Kozak M. J Biol Chem. 1991 25; 266 (30):19867-70]) and termination signals [Kochetov A V et al. FEBS Lett. 1998 4; 440(3):351-5] were introduced.

7. Unique XhoI and NotI sites were added to the 5' and 3' termini, respectively, as presented in FIGS. 28A and 28B.

The invention is further described by the following numbered paragraphs:

1. A recombinant vesicular stomatitis virus (VSV) vector wherein the gene encoding the VSV surface glycoprotein G (VSV G) is functionally replaced by HIV Env.
2. The vector of paragraph 1 wherein the HIV Env is recognized by antibodies PG9, PG16, 2G12, b12, 2F5, 4E10 or Z13, or other Env-specific antibodies, including broad potent neutralizing trimer-specific antibodies.
3. A recombinant vesicular stomatitis virus (VSV) vector encoding a modified form of VSV G, wherein the modified form of VSV G harbors epitopes from the HIV Env membrane proximal external region (MPER).
4. The vector of paragraph 3 wherein the MPER sequence is inserted into the membrane proximal region of VSV G.
5. The vector of paragraph 3 or 4 wherein a G-MPER protein binds with high avidity to 2F5 and 4E10 monoclonal antibodies.
6. A recombinant vesicular stomatitis virus (VSV) vector encoding a an N-terminally truncated form of VSV G (G/Stem), wherein the G/Stem presents Env epitope sequences on the surface of VSV particles.
7. The vector of paragraph 6 wherein G/Stem contains a cytoplasmic tail (CT) and trans-membrane (TM) spanning domains of G, a membrane proximal extracellular polypeptide (the Stem) that can be 0 to 16 to 68 amino acids in, wherein HIV Env epitopes are appended to the Stem.
8. The vector of paragraph 7 wherein the HIV Env epitopes are MPER epitopes.
9. The vector of paragraph 8 wherein the G/Stem-MPER molecules bind to 2F5 10 and 4E10 monoclonal antibodies with high affinity.
10. The vector of any one of paragraphs 1-9 wherein the HIV Env is a mutant HIV Env.
11. A method of generating novel chimeric EnvG molecules expressed and incorporated into VSV comprising:
    (a) serially passaging replication-competent chimeric VSV-HIV viruses that lack the capacity to encode wild-type G and are dependent on EnvG for infection and propagation on cells to promote emergence of viruses with greater replicative fitness and
    (b) identifying novel mutations that enhance Env or EnvG function.
12. The method of paragraph 11, wherein the cells are CD4/CCR5$^+$ cells.
13. The method of paragraph 11 or 12 wherein the novel mutations escalate trimer abundance on the virus particle and/or increase the stability of the functional trimeric form of Env or a chimeric EnvG.
14. The method of paragraph 11, 12 or 13 further comprising determining whether the Env or EnvG immunogens elicit broadly neutralizing anti-Env antibodies.
15. The method of paragraph 11, 12, 13 or 14 further comprising applying selective pressure to generate novel Env or EnvG molecules expressed and incorporated into VSV, wherein the selective pressure is binding to an antibody of interest.
16. The method of paragraph 15 wherein the antibody is PG9, PG16, b12, 2G12, 2F5 or 4E10 or any other broad potent neutralizing Env trimer specific antibody.
17. A method of producing an immune response comprising administering to a mammal the vector of any one of paragraphs 1-10.
18. A method of eliciting an immune response comprising administering to a mammal the vector of any one of paragraphs 1-10.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A recombinant vesicular stomatitis virus (VSV) vector wherein the gene encoding the VSV surface glycoprotein G (VSV G) comprises a polynucleotide encoding a polypeptide comprising:

a transmembrane domain;

a cytoplasmic tail; and an ectodomain comprising a stem region, wherein the ectodomain, and not the transmembrane domain, comprises one or more HIV Env gp41 membrane-proximal external region (MPER) epitopes, and wherein the stem region comprises the amino acid sequence of one or more of SEQ ID NO: 3, SEQ ID NO: 4, SEQ ID NO: 5, SEQ ID NO: 8, SEQ ID NO: 11 and SEQ ID NO: 12.

2. The vector of claim 1 wherein the HIV Env Epitope is recognized by antibodies PG9, PG16, 2G12, b12, 2F5, 4E10 or Z13, or other Env-specific antibodies, including broad potent neutralizing trimer-specific antibodies.

3. A vaccine comprising the vector of claim 1.

4. The vaccine of claim 3, wherein the vaccine is an intramuscular or mucosal vaccine.

5. A method of producing an immune response or eliciting an immune response against HIV comprising administering to a mammal the VSV vector of claim 1.

6. The method of claim 5, wherein the HIV Env Epitope is recognized by a PG9, PG16, 2G12, b12, F15, 4E10, Z13 or a broadly neutralizing trimer-specific antibody.

7. The method of claim 5, wherein the vector is administered to a nasal and/or oral cavity.

8. The method of claim 5, wherein the vector is administered over a vaccine schedule from about 0 to 8 weeks.

9. The vector of claim 1, wherein the stem region comprises the amino acid sequence of one or more of SEQ ID NO: 3, SEQ ID NO: 4, and SEQ ID NO: 9.

10. The vector of claim 1, wherein the stem region comprises the amino acid sequence of SEQ ID NO: 5, SEQ ID NO: 8, SEQ ID NO: 11, or SEQ ID NO: 12.

11. The vector of claim 1, wherein the stem region comprises 68, 42, or 16 amino acids.

* * * * *